United States Patent
Cox et al.

(10) Patent No.: US 6,283,991 B1
(45) Date of Patent: Sep. 4, 2001

(54) ENDOLUMINAL PROSTHESES AND THERAPIES FOR HIGHLY VARIABLE BODY LUMENS

(75) Inventors: Brian Cox, Cupertino; Michael A. Evans, Palo Alto; Allan Will, Atherton; Jay A. Lenker, Los Altos Hills; Steven W. Kim, Sunnyvale; Kirsten Freislinger, Menlo Park, all of CA (US)

(73) Assignee: Medtronics Inc., Minneapolis, MN (US)

( * ) Notice: Subject to any disclaimer, the term of this patent is extended or adjusted under 35 U.S.C. 154(b) by 0 days.

(21) Appl. No.: 09/121,226

(22) Filed: Jul. 22, 1998

Related U.S. Application Data

(63) Continuation of application No. 08/615,697, filed on Mar. 13, 1996, now Pat. No. 5,824,040.
(60) Provisional application No. 60/008,254, filed on Dec. 1, 1995.

(51) Int. Cl.⁷ .................................................. A61F 2/00
(52) U.S. Cl. .......................................... 623/1.13; 623/1.44
(58) Field of Search ................................. 623/1.11, 1.13, 623/1.22, 1.44

(56) References Cited

U.S. PATENT DOCUMENTS

| 3,945,052 | 3/1976 | Liebig . |
| 4,130,904 | * 12/1978 | Whalen .............................. 623/1.13 |

(List continued on next page.)

FOREIGN PATENT DOCUMENTS

| 0 357 003 A2 | 3/1990 | (EP) . |
| 0 472 731 A1 | 3/1992 | (EP) . |
| 0 506 918 B1 | 10/1992 | (EP) . |
| 0 508 473 A2 | 10/1992 | (EP) . |
| 0 551 179 A1 | 7/1993 | (EP) . |
| 0 646 365 A1 | 4/1995 | (EP) . |

(List continued on next page.)

OTHER PUBLICATIONS

Chuter, et al., "Anatomy of the Infrarenal Aortic Aneurysm," Endolumninal Vascular Prostheses, pp. 21–36; Little Brown and Company; Boston (1995).

Donayre, et al., "Patient Selection and Preoperative Assessment," Endoluminal Vascular Prostheses, pp. 255–283; Little Brown and Company (1995).

World Medical Manufacturing Corporation Internet Web Page Information, downloaded Aug. 4, 1997.

*Primary Examiner*—Michael J. Milano
(74) *Attorney, Agent, or Firm*—Sterne, Kessler, Goldstein & Fox PLLC

(57) ABSTRACT

The present invention provides a branching endoluminal prosthesis for use in branching body lumen systems which includes a trunk lumen and first and second branch lumens. The prostheses comprises a radially expandable tubular trunk portion having a prosthetic trunk lumen, and radially expandable tubular first and second branch portions with first and second prosthetic branch lumens, respectively. A radially expandable tubular Y-connector portion provides fluid communication between the prosthetic trunk lumen and the first and second prosthetic branch lumens. Although it is often considered desirable to maximize the column strength of endoluminal prostheses, and although the trunk portion will generally have a larger cross-section than much of the remainder of a branching endoluminal prostheses, the expanded trunk portion is more axially flexible than the expanded Y-connector portion, as insufficient flexibility along the trunk portion may result in leakage between the prosthesis and the trunk lumen of the body lumen system. In contrast, the Y-connector portion benefits form a less axially flexible structure to avoid distortion of the flow balance between the luminal branches.

14 Claims, 22 Drawing Sheets

U.S. PATENT DOCUMENTS

| | | |
|---|---|---|
| 4,503,569 | 3/1985 | Dotter . |
| 4,512,338 | 4/1985 | Balko et al. . |
| 4,550,447 | 11/1985 | Seiler, Jr. et al. . |
| 4,647,416 | 3/1987 | Seiler, Jr. et al. . |
| 4,718,907 | 1/1988 | Karwoski et al. . |
| 4,728,328 | 3/1988 | Hughes et al. . |
| 4,774,949 | 10/1988 | Fogarty . |
| 4,820,298 | 4/1989 | Leveen et al. . |
| 4,957,508 | 9/1990 | Kaneko et al. . |
| 5,019,090 | 5/1991 | Pinchuk . |
| 5,035,706 | 7/1991 | Giantureo et al. . |
| 5,064,435 | 11/1991 | Porter . |
| 5,078,726 | 1/1992 | Kreamer . |
| 5,122,154 * | 6/1992 | Rhodes ............................ 606/198 |
| 5,123,917 * | 6/1992 | Lee ...................................... 623/1 |
| 5,151,105 | 9/1992 | Kwan-Gett . |
| 5,163,958 | 11/1992 | Pinchuk . |
| 5,211,658 | 5/1993 | Clouse . |
| 5,219,355 | 6/1993 | Parodi et al. . |
| 5,226,913 | 7/1993 | Pinchuk . |
| 5,229,045 | 7/1993 | Soldani . |
| 5,282,823 * | 2/1994 | Schwartz ............................ 623/1 |
| 5,282,824 | 2/1994 | Giantureo . |
| 5,282,847 | 2/1994 | Trescony et al. . |
| 5,316,023 | 5/1994 | Palmaz et al. . |
| 5,330,500 | 7/1994 | Song . |
| 5,366,504 | 11/1994 | Andersen et al. . |
| 5,370,683 | 12/1994 | Fontaine . |
| 5,387,621 | 2/1995 | Soldani . |
| 5,397,345 | 3/1995 | Lazaurs . |
| 5,405,377 * | 4/1995 | Cragg ................................. 623/1 |
| 5,425,765 | 6/1995 | Tiefenbrun et al. . |
| 5,443,496 | 8/1995 | Schwartz et al. . |
| 5,443,499 | 8/1995 | Schmitt . |
| 5,456,713 | 10/1995 | Chuter . |
| 5,476,506 | 12/1995 | Lunn . |
| 5,507,767 | 4/1996 | Maeda et al. . |
| 5,507,769 | 4/1996 | Marin et al. . |
| 5,514,178 | 5/1996 | Torchio . |
| 5,545,210 | 8/1996 | Hess et al. . |
| 5,545,220 | 8/1996 | Andrews et al. . |
| 5,556,426 | 9/1996 | Popadiuk et al. . |
| 5,562,724 | 10/1996 | Vorwerk et al. . |
| 5,609,627 | 3/1997 | Goicoechea et al. . |
| 5,617,878 | 4/1997 | Taheri . |
| 5,632,763 | 5/1997 | Glastra . |
| 5,632,772 | 5/1997 | Alcime et al. . |
| 5,653,743 | 8/1997 | Martin . |
| 5,662,675 * | 9/1997 | Polanskyj-Stockert ............ 623/1 |
| 5,676,697 | 10/1997 | McDonald . |
| 5,733,325 | 3/1998 | Robinson et al. . |
| 5,843,166 * | 12/1998 | Lentz ............................. 623/1.13 |
| 5,851,232 * | 12/1998 | Lois ............................... 623/1.13 |
| 6,165,212 * | 2/2000 | Dereume ....................... 623/1.13 |
| 6,168,619 * | 1/2001 | Dinh ............................. 623/1.13 |
| 6,214,040 * | 4/2001 | Jayaraman .................... 623/1.13 |

FOREIGN PATENT DOCUMENTS

| | | |
|---|---|---|
| 0 684 022 A2 | 11/1995 | (EP) . |
| 0 421 729 B1 | 1/1996 | (EP) . |
| 0 689 805 A2 | 1/1996 | (EP) . |
| 0 722 702 A1 | 7/1996 | (EP) . |
| 2 678 508 | 1/1993 | (FR) . |
| 1457921 A1 | 2/1989 | (RU) . |
| WO 95/05132 | 2/1995 | (WO) . |
| WO 95/08966 | 4/1995 | (WO) . |
| WO 95/09586 | 4/1995 | (WO) . |
| WO 95/16406 | 6/1995 | (WO) . |
| WO 95/18585 | 7/1995 | (WO) . |
| WO 95/23563 | 9/1995 | (WO) . |
| WO 95/26695 | 10/1995 | (WO) . |
| WO 95/29646 | 11/1995 | (WO) . |
| WO 95/34255 | 12/1995 | (WO) . |
| WO 96/00103 | 1/1996 | (WO) . |
| WO 96/03092 A1 | 2/1996 | (WO) . |
| WO 96/23455 | 8/1996 | (WO) . |

* cited by examiner

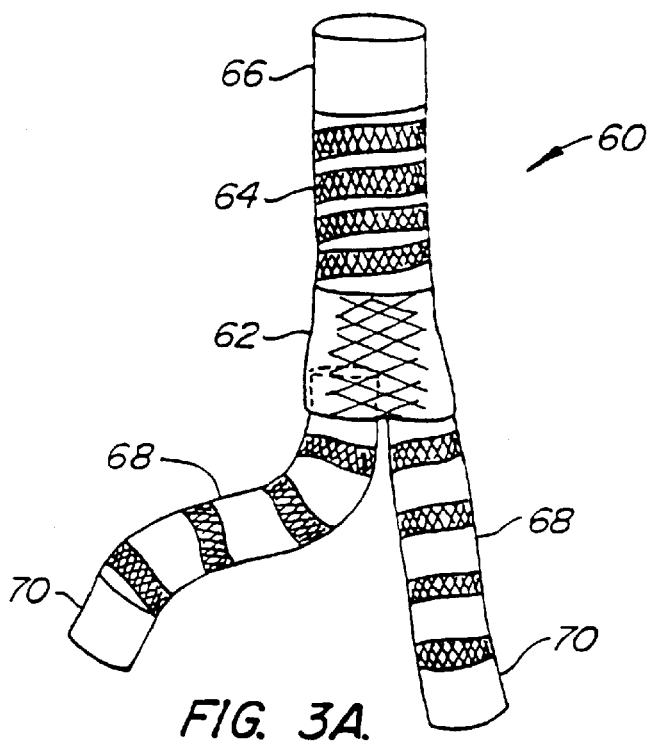
FIG. 3A.
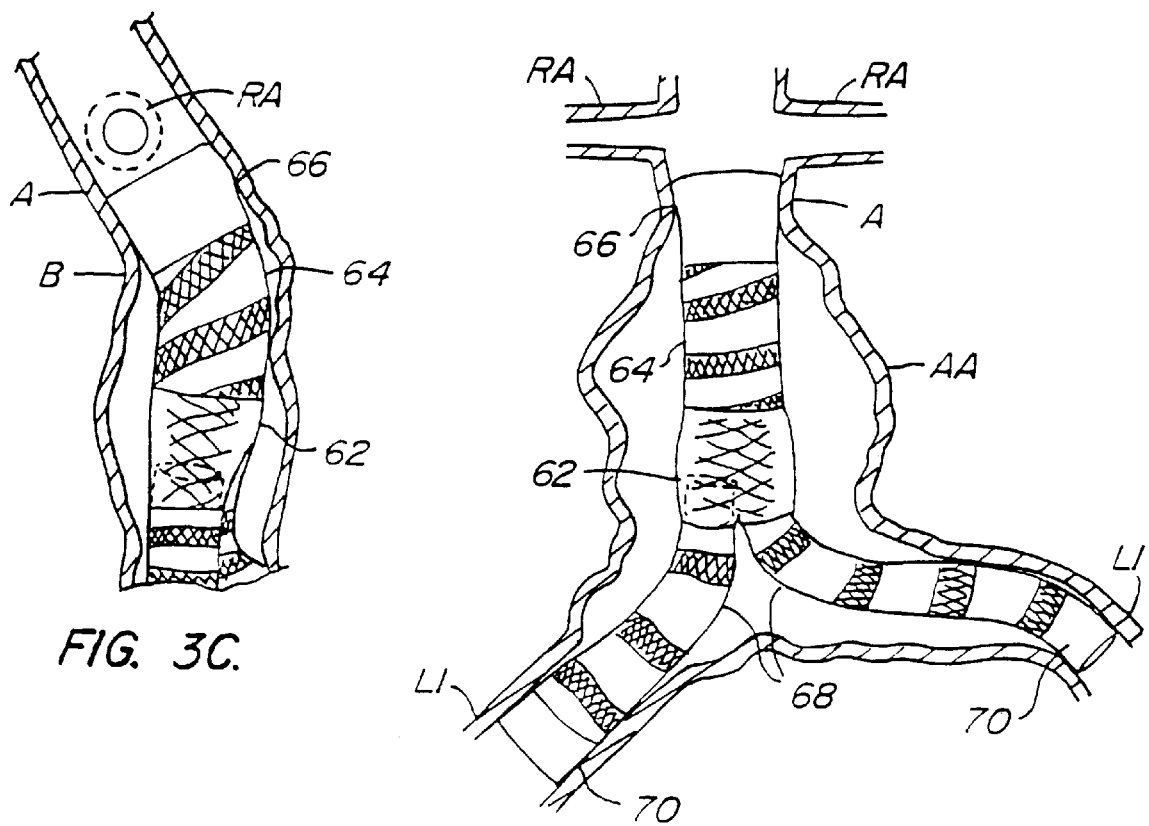
FIG. 3C.
FIG. 3B.

ENDOLUMINAL PROSTHESES AND THERAPIES FOR HIGHLY VARIABLE BODY LUMENS

CROSS-REFERENCE TO RELATED APPLICATION

This application is a continuation of U.S. patent application Ser. No. 08/615,697, filed Mar. 13, 1996 now U.S. Pat. No. 5,824,040, which is a continuation-in-part of provisional U.S. patent application Ser. No. 60/008,254, filed Dec. 1, 1995, the full disclosure of which is incorporate herein by reference.

BACKGROUND OF THE INVENTION

1. Field of the Invention

The present invention relates generally to tubular prostheses, such as grafts, stents, stent-grafts, and the like. More particularly, the present invention provides radially expandable tubular prosthetic structures which are deployable within tortuous body lumens, particularly within branching blood vessels for the treatment of abdominal and other aneurysms.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms are most commonly treated in open surgical procedures, where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 2% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from undesirable limitations. In particular, proper matching of an endovascular prosthesis with the complex and highly variable vascular geometry can be problematic.

Proper matching of the prosthesis to the proximal neck of the aortic vessel and the branching blood vessels is critical to the treatment of an aneurysm. The prosthesis preferably extends axially beyond the weakened portion of the blood vessel to anchor securely in the less diseased vessel wall. To prevent the leakage of blood through a ruptured aneurysm, and also to prevent the release of thrombus from within the distended aneurysm and into the bloodstream, it is also preferable that the prosthetic lumen be substantially sealed against the healthy endothelium. The prosthetic lumen should remain open despite physiological movement of the vasculature and environmental stresses, so as to promote the free flow of blood. Furthermore, the geometry of the prosthetic lumen at the luminal intersection where the abdominal aorta meets the iliac arteries is of particular importance, as this bifurcation can have a significant impact on the relative blood flows through the two iliac arteries.

Unfortunately, the size, extent, and specific geometry of abdominal aortic aneurysms can vary widely from patient to patient. While the aneurysm is often downstream of the renal arteries, as noted above, it may begin in very close proximity to these lateral branching blood vessels, and in some cases will extend up to, above, and along the renals themselves. Additionally, while the aneurysm itself is typically a distension of the vessel wall, the path the prosthesis must follow within the diseased vessel may be fairly convoluted. For example, the abdominal aorta typically defines a significant bend between the renal arteries and the iliac arch when viewed from a lateral position. This aortic bend often remains quite pronounced despite the presence of the distended aneurysm, and complicates the sealing and anchoring of the endoluminal prosthesis adjacent the renal arteries.

Abdominal aortic aneurysms also appear to have a significant effect on the geometry of the intersection between the abdominal aorta and iliac arteries. Even among healthy patients, there are significant variations in the angles defined by the iliac arteries relative to the aorta, typically being anywhere in the range between 15–45°. The variation in aorta iliac angularity is often much wider in patients seeking therapy for aneurysms. In fact, iliac arteries which branch off from an aorta with a local angle of over 90° have been found in aneurysm patients.

Known branching endoluminal prostheses are generally formed as tubular, radially expandable stent-grafts. In contrast with the convoluted branchings of diseased body lumens, these stent-graft structures have typically been formed with simplistic cylindrical frames or "stents." A separate liner or "graft" is typically attached to the frame to prevent blood flow through a ruptured vessel wall. Such liners are often formed from inelastic fabrics to prevent pressure from distending a weakened luminal wall. Typically, these branching structures are primarily supported from immediately below the renal arteries. Patients may not be eligible for these known endovascular aneurysm therapies if this portion of the aorta is weakened by disease.

The branching stent-graft structures of the prior art have generally comprised uniform structures, in which the smaller iliac branch portions form cylinders which are substantially parallel to the aortic portion when the prosthesis is at rest. Although these straight branching prostheses are intended to deform somewhat to accommodate the branch angles of body lumen systems, the imposition of substantial axial bends on known endovascular stent-grafts tends to cause folding, kinking, or wrinkling which occludes their lumens and degrades their therapeutic value. Still another disadvantage of known bifurcated stent-grafts is that even when they are flexed to accommodate varying branch geometry, the prosthetic bifurcation becomes distorted, creating an unbalanced flow to the branches. To overcome these limitations, it has often been necessary to limit these highly advantageous, minimally invasive endovascular therapies to patients having vascular geometries and abdominal aortic aneurysms which fall within very narrow guidelines.

For these reasons, it would be desirable to provide improved endoluminal prostheses and methods for their use.

It would further be desirable to provide improved branching endoluminal prostheses, and improved methods for placement of such prostheses. It would be particularly desirable to provide endoluminal prostheses (and methods for deploying them) which would accommodate widely varying lumen system geometries, and which would thereby increase the proportion of patients eligible to receive these highly advantageous endoluminal prosthetic therapies for treatment of abdominal aortic aneurysms and other disease conditions of the body lumen systems.

2. Description of the Background Art

U.S. patent application Ser. No. 08/538,706, filed Oct. 3, 1995, now U.S. Pat. No. 5,824,037 the full disclosure of which is hereby incorporated by reference, describes modular prostheses and construction methods. Parent Provisional Application Ser. No. 60/008,254, previously incorporated herein by reference, describes bifurcated modular prosthetic structures and methods for assembling them in situ.

U.S. Pat. No. 5,064,435 describes a self-expanding prosthesis which maintains a stable axial length during radial expansion by anchoring of radial outward flares at each end, and by sliding of an overlapping medial region therebetween. U.S. Pat. No. 5,211,658 describes a method and device for endovascular repair of an aneurysm which makes use of separately introduced frame and liner structures. A similar method of repairing blood vessels is described in U.S. Pat. No. 5,078,726, in which a locking stent is expanded within a vascular graft which has been positioned within the blood vessel. The in situ deployment of an aortic intraluminal prosthesis by a catheter having two inflatable balloons is described in U.S. Pat. No. 5,219,355.

European patent application publication no. 0 551 179 describes a method for deploying two tubular grafts which extend in parallel from the renals and into the aorta. U.S. Pat. No. 5,360,443 describes a bifurcated aortic graft which is secured to the aorta by a plastically deformable frame positioned between the renal arteries and the iliacs. Soviet Patent 145-921 describes a bifurcated blood vessel prosthesis having a fastening element which extends past the renal arteries to prevent migration. U.S. Pat. No. 4,774,949 describes a catheter having a lumen adapted to access branch arteries.

U.S. Pat. Nos. 4,550,447 and 4,647,416 describe vascular PTFE grafts which include transverse ribs integral with a tube wall, and methods for their production. U.S. Pat. No. 5,443,499 describes a radially expandable tubular prostheses for intraluminal implantation within children. U.S. Pat. Nos. 5,229,045 and 5,387,621 describe porous membranes based on unstable polymer solutions which are suitable for vascular prostheses, and methods for their production.

SUMMARY OF THE INVENTION

In a first aspect, the present invention provides a branching intraluminal prostheses for use in a branching body lumen system that includes a trunk lumen and first and second branch lumens. The prostheses comprises a radially expandable tubular trunk portion having a prosthetic trunk lumen, and radially expandable tubular first and second branch portions with first and second prosthetic branch lumens, respectively. A radially expandable tubular lumen separation portion provides fluid communication between the prosthetic trunk lumen and the first and second prosthetic branch lumens. Surprisingly, the expanded trunk portion is preferably more axially flexible than the lumen separation portion.

Although it is often considered desirable to maximize the column strength of endoluminal prostheses, and although the trunk portion will generally have a larger cross-section than much of the remainder of a branching endoluminal prostheses, in connection with the present invention it has been found that insufficient flexibility along the trunk portion may result in leakage between a bifurcated prosthesis and the trunk lumen of the body lumen system. Specifically, leaks will be produced between known uniform bifurcated prostheses and the dorsal bend which is typically found immediately downstream of the renal arteries along the abdominal aorta. On the other hand, the lumen separation portion benefits from a less axially flexible structure to avoid distortion of the flow balance between the luminal branches when conforming the prosthetic geometry to a torturous body lumen system. The present invention therefore provides non-uniform prosthetic structures which are locally optimized to meet these contradictory requirements.

Preferably, a trunk sealing cuff is provided opposite the Y-connector to seal between the prosthetic trunk lumen and the trunk lumen of the body lumen system. Similarly, the first and second branch portions are also more axially flexible than the lumen separation portion, and ideally include branch sealing cuffs opposite the lumen separation. These sealing cuffs may also benefit from relatively stiff structures, particularly where they help to anchor the prosthesis within the body lumen. The resulting prosthetic structure separates the luminal sealing, the axial conforming, and the flow separating functions of the branching prostheses to distinct axial portions of the prosthetic structure, allowing these portions to be still further independently optimized.

In another aspect, the present invention provides an endoluminal prosthesis comprising first and second prosthesis portions including first and second radially expandable frames defining first and second axes, respectively. The frames support tubular liners having lumens. A flexible joint between the first and second prosthesis portions provides open fluid communication between the first and second lumens when the first and second axes are at an angle, the flexible joint comprising a self-supporting liner which includes a polymer tube having integral ribs.

In yet another aspect, the present invention provides an endoluminal prosthesis comprising a radially expandable tubular liner having a lumen which defines an axis. A helical coil supports the liner, the coil defining a plurality of loops which are separated to enhance the axial flexibility of the prosthesis. The helical coil elongates during expansion of the liner to avoid unwinding of the coil relative to the liner. Hence, the coil may be attached at a plurality of attachment locations along the length of the coil. Preferably, the coil comprises linked diamond shaped elements, which may expand either resiliently or plastically during deployment.

In yet another aspect, the present invention provides an endoluminal prostheses for use in a body lumen, the prostheses comprising a radially expandable tubular frame having an axis. The frame includes a plurality of resiliently expandable loops, and also includes a plurality of plastically deformable connector elements extending between adjacent loops to allow the axis to conform to the body lumen.

Preferably, the connector elements plastically deform at a predetermined load which is greater than environmental forces imposed on the expanded prostheses by the surrounding body lumen, but which predetermined load is preferably less than or equal to forces imposed on the prostheses during deployment. Ideally, the adjacent loops of the frame are axially separated, and the connector elements combine serpentine structures which extend axially between the adjacent loops. It should be understood that connector elements which yieldingly bend, and which remain bent without resiliently straightening in situ will be "plastically deformed" as used herein. Hence, shape memory alloys or polymers which are deformed in situ such that they will not recover their original shape at body temperatures will be "plastically deformed", even if they would recover their shape if removed from the patient body and heated beyond a transition temperature.

In some embodiments, at least some of the connector elements are attached to an associated loop of the frame using axially oriented slots, loosely tied sutures, or some other attachment mechanism which allows a limited amount of axial motion without deforming the connector member. Advantageously, such a structure provides a self-expanding prostheses which conforms to a torturous axial path of a body lumen without imposing resilient straightening forces. This structure is therefore particularly well suited for use in the flexible trunk or branch portions of the branching prosthesis described above.

In yet another aspect, the present invention provides a bifurcated endoluminal prosthesis for use within a branching body lumen system having a trunk lumen and first and second branch lumens. The trunk lumen will have a larger cross-section than the branch lumens, and the trunk and branch lumens will be in fluid communication at a luminal intersection. The prostheses comprises a hub module which is deployable within the body lumen system adjacent the lumenal intersection. A trunk module includes a first port which sealingly engages the hub module when radially expanded therein. An end opposing the first port seals radially against the surrounding trunk lumen opposite the hub module. A prosthetic trunk lumen is provided between the first port and the sealing end. Such a structure is particularly advantageous when the trunk lumen of the body lumen system has been weakened by disease adjacent to or beyond the lumenal intersection, as the hub module facilitates sealing at the bifurcation. Preferably, the hub module comprises a tubalar wall material which is at least partially self-supporting, wherein a portion of the hub between the trunk lumen port and at least one of the first and second branch ports has an enhanced axial flexibility. Optionally, a radially expandable branch module sealingly engages the deployed first branch port of the hub module, and extends along the first branch lumen of the body lumen system away from the luminal intersection. In certain patients, for example, those having aorta iliac regions which are highly distorted by an aneurism, it may be advantageous to form the hub module as a custom molded tubular expandable body wherein the trunk port and branch ports substantially match the trunk lumen in first and second branch lumens of that particular patient's body lumen system.

In yet another aspect, the present invention provides a bifurcated endoluminal prosthesis for use within a branching body lumen system having a trunk lumen and first and second branch lumens. The trunk lumen will have a larger cross-section than the branch lumens, and the trunk and branch lumens will be in fluid communication at a luminal intersection. The prostheses comprises a branch module having a first branch end which is expandable within the first branch of the body lumen system, and also having a second branch end which is expandable within the second branch of the body lumen system, while a branch lumen extends therebetween. A trunk port is located between the first and second branch ends, the trunk port is sealingly engageable with a first end of a tubular trunk module. A second end of the trunk module seals radially against the surrounding trunk lumen of the body lumen system. This branch module is particularly advantageous for use in body lumen systems having relatively sharp trunk/branch angles, particularly for installation across the two iliac arteries in patients having relatively advanced aortic aneurysms.

In yet another aspect, the present invention provides a bifurcated endoluminal prosthesis for use within a branching body lumen system having a trunk lumen and first and second branch lumens. The trunk lumen will have a larger cross-section than the branch lumens, and the trunk and branch lumens will be in fluid communication at a luminal intersection. The prostheses comprises a primary module deployable adjacent the luminal intersection, and a tubular trunk lumen which is supported at least in part by the primary module when expanded therein. Advantageously, this structure allows the prostheses to be supported for adjacent healthy branch lumens, for example, allowing endovascular prosthetic therapies for patient's who have relatively healthy iliac arteries, but who do not have sufficiently healthy aortal wall to substantially support a prostheses from between the renal arteries and the iliacs. Alternatively, the primary module comprises a tubular first branch module which supports the trunk module from within the first branch lumen of the body lumen system.

In yet another aspect, the present invention provides a bifurcated endoluminal prostheses comprising a radially expandable trunk portion having a trunk lumen and a branch end. Radially expandable first and second branch portions extend from the branch end of the trunk portion, with first and second branch lumens, respectively. The first and second branch lumens are in fluid communication with the trunk lumen of the trunk portion, and at least one of the branch portions is compressible within the trunk portion and extendible from the trunk portion when the prostheses is positioned in situ. The at least one extendible branch portion preferably comprises an evertable self-supporting or composite structure. Alternatively, the at least one extendible branch portion may slidingly engage the radially expandable trunk portion so that it can telescope into the deployed position after the trunk portion is positioned.

The present invention further provides a method for deploying and endoluminal prostheses in a branching body lumen system which includes a trunk lumen and first and second branch lumens. The trunk and branch lumens are in fluid communication at a luminal intersection, the trunk lumen being larger in cross-section than the branch lumens. The method comprises deploying a primary module within the body lumen system adjacent the luminal intersection so that a trunk portion of the primary module extends along the trunk lumen. A trunk module is then expanded within the trunk lumen while an end of the trunk module is within the trunk port of the primary module. Hence, the primary module engages and supports the trunk module, rather than relying substantially entirely on the trunk lumen of the body lumen system for support.

In another aspect, the present invention provides a method for deploying an endoluminal prothesis in a branching body lumen system which includes a trunk lumen and first and second branch lumens which are in fluid communication at a luminal intersection. The method comprises positioning a tubular prosthetic branch module across the luminal intersection from the first branch into the second branch so that a trunk port of the branch prostheses module is adjacent to the luminal intersection. The positioned branch module is expanded, and a tubular trunk module is positioned within the trunk lumen of the body lumen system with at least one opening adjacent the luminal intersection. The positioned trunk module is expanded, wherein expansion of the ladder of the branch module and the trunk module sealingly engages the branch and trunk modules together.

In yet another aspect, the present invention provides a method for deploying an endoluminal prothesis in a branching body lumen system of a patient, the branching lumen system including first, second and third lumens in fluid communication at a luminal intersection. The method comprises positioning a first guide wire through the luminal intersection by introducing the first wire in through the first lumen and out the second lumen. A distal end of the first wire is threaded through a distal opening of a second guide wire. The prostheses may be positioned by selectively tensioning proximal and distal ends of the first wire, and by selectively tensioning the proximal end of the second wire. Optionally, the threaded first wire is returned through the intersection, and the distal end of the second wire is advanced toward the intersection by tensioning the proximal and distal ends of the first wire. Ideally, the first wire is returned back along the second lumen to the intersection, and then out of the patient through the third lumen, allowing the prosthesis to be precisely positioned by tension from each of the three lumens at the luminal intersection.

In yet another aspect, the present invention provides a method for producing an endoluminal prosthesis comprising attaching an axially compressible elongate structure to an elongate liner strip and coiling the strip to form a helix having a plurality of loops. The adjacent loops may conveniently be attached to form a tube, thereby allowing continuous and automated production of large numbers of coil-supported prostheses.

In a penultimate aspect, the present invention provides a sealing structure for sealing an end of a tubular endoluminal prosthesis against a plurality of flexible sealing flaps extending from the prosthesis adjacent the end. The sealing flaps are resiliently biased to flaps radially outward so as to independently seal against the surrounding lumen.

In a final aspect, the present invention provides an endoluminal prosthesis comprising a tubular liner and a frame supporting the tubular liner. The frame defines a plurality of loops having axially oriented apices, at least some of these adjacent apices on adjacent loops being offset to enhance axial flexibility of the prosthesis.

BRIEF DESCRIPTION OF THE DRAWINGS

FIGS. 3A–3C illustrate a bifurcated endovascular prosthesis having a relatively rigid expanded Y-connector portion, axially flexible branch and trunk portions, and sealing/anchoring cuffs, according to the principles of the present invention.

DESCRIPTION OF THE SPECIFIC EMBODIMENTS

The present invention provides radially expansible tubular prostheses, particularly grafts, stents, and stent-grafts, which are highly adaptable to varying luminal system geometries. The prostheses of the present invention are suitable for a wide variety of therapeutic uses, including stenting of the ureter, urethra, trachea, branchi, esophagus, biliary tract, and the like. The present devices and methods will also be useful for the creating of temporary or long term lumens, such as the formation of fistulas.

The prosthetic structures of the present invention will find their most immediate use as endovascular prostheses for the treatment of diseases of the vasculature, particularly aneurysms, stenoses, and the like, and are especially well suited to the distorted aortal/iliac junction of persons having advanced vascular diseases. These prostheses will generally be radially expansible from a narrow diameter configuration to facilitate introduction into the body lumen, typically during surgical cutdown or percutaneous introduction procedures.

The prosthetic structures described hereinbelow will find use in axially uniform cylindrical prostheses, in preassembled bifurcated prostheses, and as prosthetic modules which are suitable for selective assembly either prior to deployment, or in situ. Such selective assembly of prosthetic modules to form a customized endoluminal prosthesis is more fully described in U.S. patent application Ser. Nos. 60/008,254 and 08/538,706 , now U.S. Pat. No. 5,824,037, the full disclosures of which have previously been incorporated herein by reference.

Figure 1:
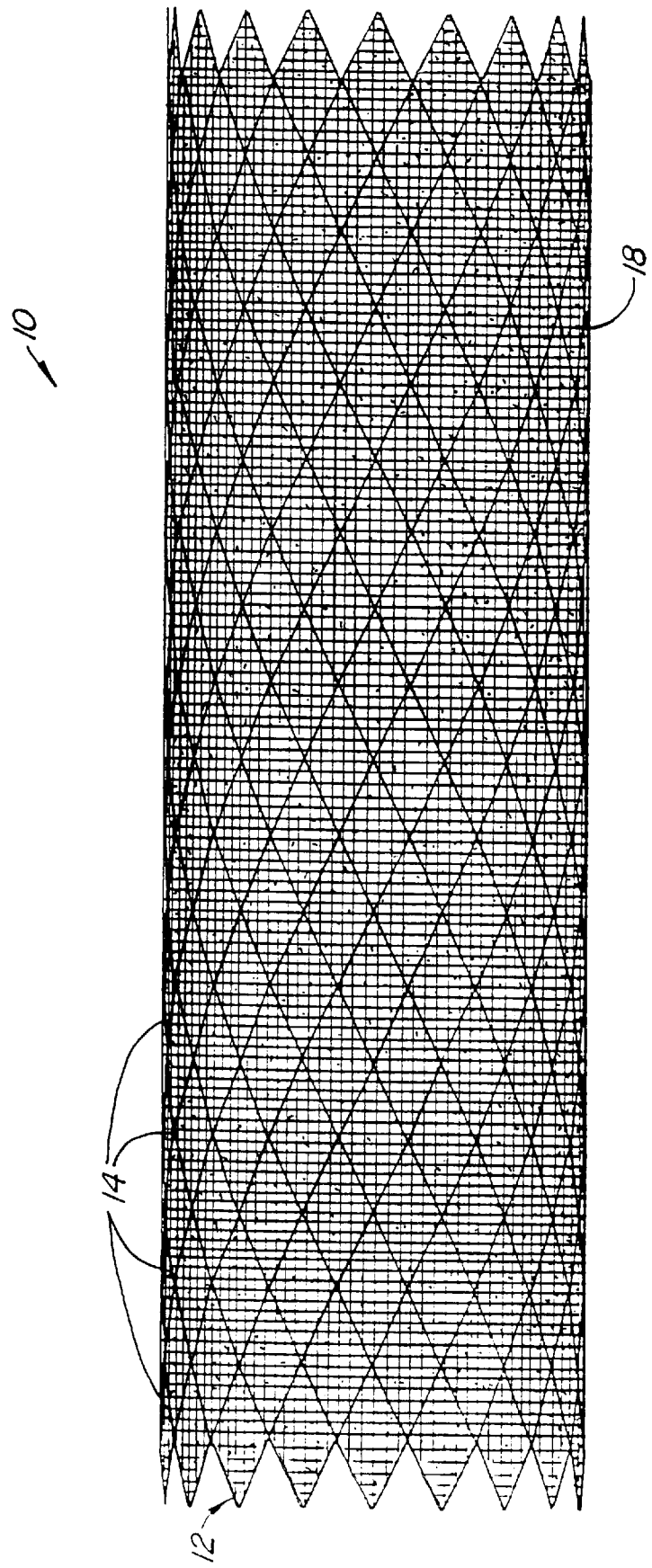
FIG. 1 is a side view of an exemplary cylindrical vascular stent-graft having axially constant characteristics.

An exemplary cylindrical graft structure 10 is illustrated in FIG. 1. Prosthesis 10 comprises a perforate tubular frame 12 which includes a plurality of independent (non-connected) ring frames 14. The tubular frame 12 supports an inner liner 18. Optionally, an outer liner is disposed over the ring frames, either inside of inner liner 18, or in combination therewith.

To secure ring frames 14 in place, and to secure the liner to the perforate tubular frame 12, the liner is typically sutured to the frame. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other.

The prosthesis 10 will typically have a length in the range from about 20 mm to 500 mm, preferably from 50 mm to 200 mm, with a relaxed diameter in the range from about 4 mm to 45 mm, preferably being in the range from about 5 mm to 38 mm. Alternative stent-graft structures are more fully described in application Ser. No. 08/538,706, now U.S. Pat. No. 5,824,037, previously incorporated by reference.

Figure 2:
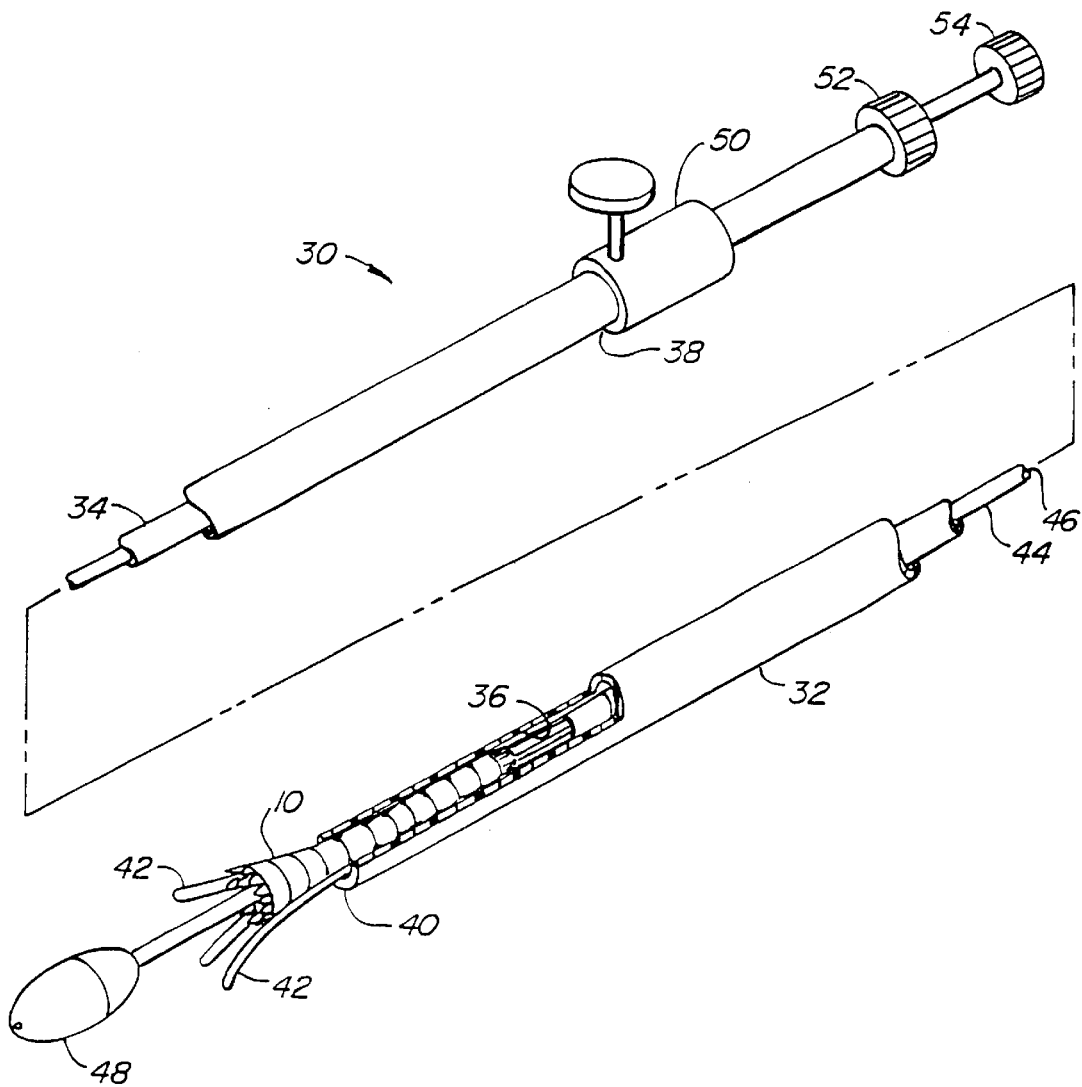
FIG. 2 is a perspective view of an exemplary delivery catheter for use with the prostheses of the present invention, with a portion of the distal end broken away to disclose a prosthesis therein.

Referring now to FIG. 2, an exemplary delivery catheter 30 for use with the endoluminal prostheses of the present invention comprises a tubular cover 32 and a shaft 34. Cover 32 has a central lumen 36 extending from a proximal end 38 to a distal end 40. Shaft 34 is slidably received within central lumen 36 and extends proximally of cover 32. A plurality of runners 42 extend distally from shaft 34. Runners 42 line a portion of the inner surface of lumen 36, and slide within the lumen of the shaft. Shaft 34 also has a lumen, in which a core shaft 44 is slidably disposed. Core shaft 44 has a guide wire lumen 46. Nosecone 48 is fixed to the distal end of core shaft 44, and can therefore be manipulated independently of runners 42.

Prosthesis 10 is radially compressed and restrained within the plurality of runners 42. In turn, cover 32 prevents runners 42 from expanding outward. Runners 42 are formed from a hard material, and distribute the expansion load of prosthesis 10 over the inner surface of central lumen 36. The deploying force is applied proximally against a slider 50 attached to a distal end 38 of cover 30, while holding a luer fitting 52 at the distal end of shaft 34, thereby withdrawing the cover proximally from over the prostheses. An additional luer adapter 54 at the distal end of core shaft 44 allows the core shaft to be manipulated independently, and to be releasibly secured to the shaft 34. Exemplary methods and devices for placement of the prostheses of the present invention are more fully described in U.S. patent application Ser. No. 08/475,200, filed Jun. 7, 1995 now U.S. Pat. No. 5,683,451, the full disclosure of which is incorporated herein by reference.

Referring now to FIGS. 3A–3C, an exemplary branching endovascular prothesis 60 comprises a lumen separation portion 62 between a trunk portion 64 and two branch portions 68. Lumen separation portion 62 preferably comprises a relatively rigid structure, having higher column and hoop strength than the remainder of the prosthesis.

In this exemplary embodiment, the lumen separation portion comprises a flexible liner supported by a resiliently expanding frame. The cross-section of the frame adjacent the branches includes discrete lobes which correspond to the first and second branches, and also includes an isthmus therebetween to help prevent an imbalance of flow from the trunk portion to the branch portions. Such a lumen separation portion is more fully described in parent application a previously incorporated by reference. Ideally, the perforate frame of lumen separation portion 62 is continuous along its axial length, increasing the column strength of the lumen separation so that the flow separation geometry of the branching inner lumen remains constant regardless of the flexing of the trunk and/or branch portions.

The advantageous flexibility of branch portions 68 is shown most clearly in FIG. 3B, in which prostheses 60 is shown deployed within an abdominal aorta A downstream of the renal arteries RA, extending beyond an abdominal aortic aneurism AA, and into the right and left iliac arteries RI, LI. Branch portions 68 have relatively high axial flexibility to accommodate the extreme angles between the iliac and abdominal arteries which have been found in patients having such aneurysms.

Trunk sealing cuff 66 and branch sealing cuffs 70 securely anchor the prostheses against the healthy tissue beyond the aneurism, and also seal the prosthetic lumen against the surrounding endothelium of the body lumen system. Trunk sealing cuff 66 will often comprise a polyester such as Dacron™, preferably in an expansible form, ideally as a fabric woven with partially oriented or unoriented polyester fibers in the fill or weave. Alternatively, polyester (or some other fiber) which has been wrapped around a core fiber to allow expansion may be used, or the sealing cuff may comprise a PTFE, silicone, or polyurethane foam to promote sealing between the prosthetic lumen and the surrounding body lumen. Exemplary sealing cuff structures are more fully described in patent application Ser. Nos. 08/525,989 and 08/538,706, filed Oct. 3, 1995, and Sep. 8, 1995, now U.S. Pat. Nos. 5,769,882 and 5,824,037, the full disclosures of which are incorporated herein by reference.

One particular advantage of the axial flexibility of trunk portion 64 can be understood with reference to the lateral view of the abdominal aorta illustrated in FIG. 3C. Although the aneurysm AA generally distends the abdominal aorta, the specific shape and extent of the aneurysm can vary widely. Even when healthy, the abdominal aorta often angles dorsally just downstream of the renal arteries. The presence of this bend B often persists despite the general distension of the abdominal aorta.

Advantageously, flexible trunk portion 64 allows the trunk sealing cuff 66 to anchor securely along the axis of the healthy abdominal aorta adjacent the renal arteries, and greatly helps to reduce perimeter leaks around the upstream end of the trunk portion. Those of skill in the art will understand that the trunk portion would tend to have a relatively high rigidity and column strength, due to its relatively large cross-section (which must accommodate the combined flow for both iliac arteries). It should also be understood that the flexible trunk and leg portions will preferably maintain sufficient hoop strength so that their respective lumens remain open throughout a wide range of branch positions, and despite normal physiological movement and environmental stress from the surrounding body lumen. Hence, the flexible trunk and leg portions will preferable comprise a coiled prosthetic structure or a radially expandable, axially malleable structure as described herein below. Alternatively, the flexible trunk and branch portions may comprise an unsupported (or self-supporting) liner.

Figure 4:
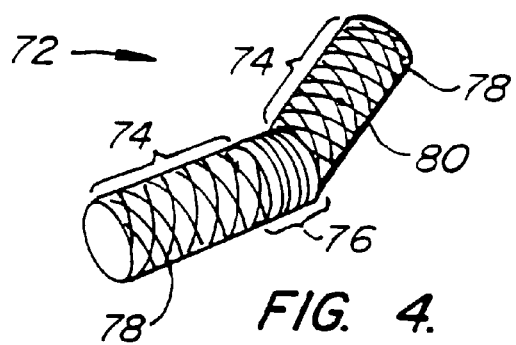
FIG. 4 illustrates a prosthesis having two stent-graft portions connected by a flexible joint comprising an integrally ribbed polymer tube.

Referring now to FIG. 4, a jointed prosthesis structure 72 provides axial flexibility and kink resistance, and may therefore find use in the flexible sections of exemplary branching endoluminal prosthesis 60 (see FIG. 3A). Jointed prosthesis 72 includes a plurality of stent-graft portions 74 with a joint portion 76 therebetween. Stent-graft portions 74 comprise a liner 80 supported by a perforate radially expandable frame 78. Preferably, joint portion 76 comprises an integrally ribbed polymer tube, as taught by U.S. Pat. Nos. 4,647,416 and 4,550,447, the full disclosures of which are incorporated herein by reference. Ideally, the joint comprises a ribbed PTFE tube which extends continuously to form the liners of the stent-graft portions.

Advantageously, the framed structure of the stent-graft portion provides the column and hoop strength to support the inner lumen, while the self-supporting joint structure allows the jointed prosthesis to easily adapt to tortuous body lumens. It may be advantageous to provide a series of such jointed stent-graft sections to allow the prosthesis to adapt to the highly tortuous arteries associated with aneurysm patients.

Figure 5A:
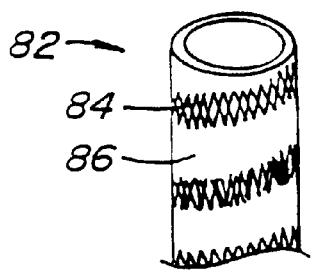
FIGS. 5A–5D illustrate an endoluminal prosthetic structure in which a frame is supported by a helical coil of expansible diamond shaped elements, for use in the flexible portions of the prosthesis of FIGS. 3A–3C.
Figure 5B:
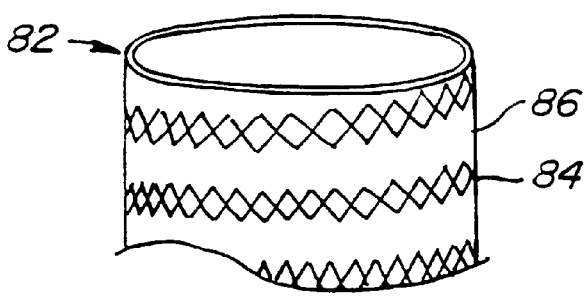
Figure 5C:
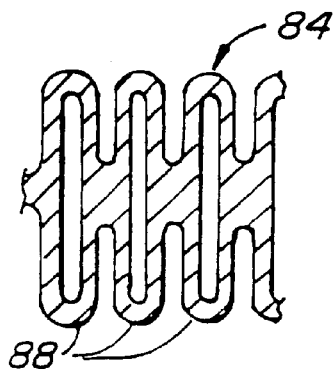

Referring now to FIGS. 5A–C, an alternative flexible prosthesis section may comprise a coil-shaped stent structure, in which the coils are separated from each other by a helical separation distance which allows the liner material to flex easily, thereby providing a prosthetic structure with both axial flexibility and hoop strength.

A limitation of known coiled expandable stent-graft structures is that they induce relative motion between the liner and support materials, the coil unwinding as the liner expands. Coiled prosthetic structure 82 overcomes this limitation by including an expandable coil 84 with an expansible liner material 86. As the prosthesis perimeter increases in size, expandable coil 84 elongates, preferably by deformation of a series of linked diamond-shaped elements 88. As the coil frame expands with the liner material, these two structures may be attached directly together at a plurality of attachment locations without binding.

The expandable coil may be either self-expanding, preferably comprising a highly resilient material, ideally comprising a shape memory alloy such as super-elastic Nitinol™, or the like. Alternatively, the coil may comprise a malleable material, typically a plastically deformable metal such as stainless steel, tantalum, martensitic shape memory alloy such as Nitinol™, a shape memory polymer, or the like.

Figure 5D:
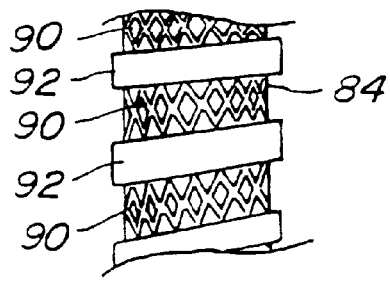

The liner will optionally be an expandable liner tube, often being a woven polyester such as Dacron™, or may alternatively comprise a plastically expansible material such as PTFE, partially oriented yarn, or an annealed or wrapped composite fiber such as those more fully described in U.S. patent application Ser. No. 08/595,944, filed Feb. 6, 1996 now U.S. Pat. No. 5,843,158, the full disclosure of which is incorporated herein by reference. Optionally, the liner tube may also include a ribbed polymer as described above. As illustrated in FIG. 5D, a ribbed PTFE liner will preferably include ribs 92 disposed between the adjacent loops 90 of expandable coil 84.

Figure 5E:
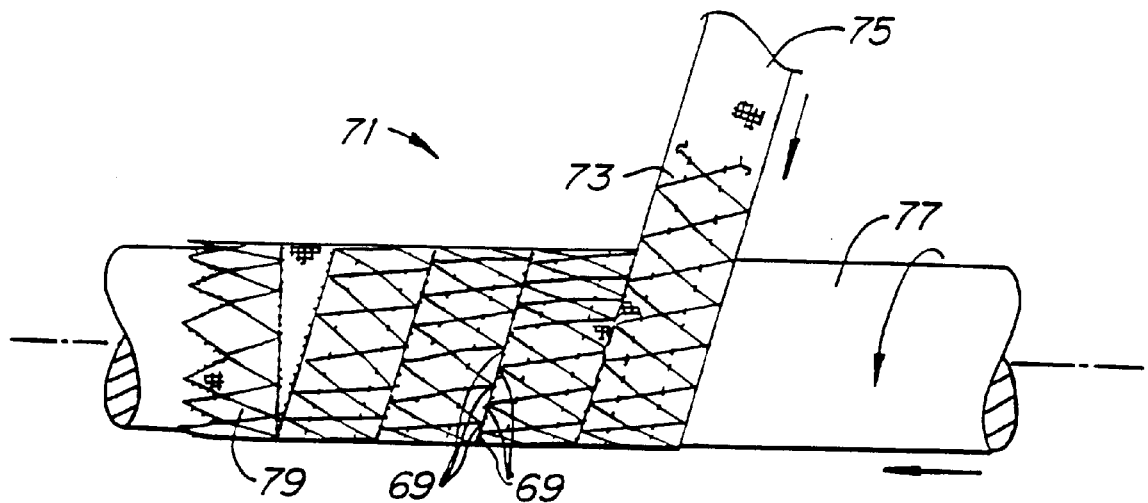
FIG. 5E illustrates a method for making an endoluminal prosthesis having a helical coil by first attaching the coil material to a strip of liner material, winding the liner strip over a mandrel, and sewing the strip in a helical shape.

A method of fabricating a helical stent-graft 71 will be described with reference to FIG. 5E. A series of linked diamond-shaped elements 73 are first attached to a strip of liner material 75, typically being stitched with a sewing machine. The ribbon is then wound over a mandrel 77 of the desired size, and adjacent edges of the ribbon are sewn to each other (or otherwise permanently joined). Such a method may be substantially automated and continuous, and is thus particularly beneficial for producing a large number of prostheses. The helical stent-graft may optionally be cut to length, but will preferably include a crown stitched stent-ring 79 for sealing and ends against a surrounding lumen when deployed therein.

A novel feature of helical stent-graft 71 which will have application in a wide range of stent-graft structures is the offsetting of apices 69. Diamond-shaped elements 73 define axially oriented apices 69 at regular intervals along the loops. Through proper sizing of mandrel 77 and monitoring of the loop sewing process, the adjacent apices may optionally be offset from the adjacent apices, each apex ideally being roughly equally spaced from the two adjacent apices as shown. Advantageously, this increases axial flexibility by allowing the liner to flex between loops but without substantially decreasing hoop strength. Conveniently, the column strength may be selectively and locally increased (and axial flexibility correspondingly decreased) by adjusting the winding of ribbon 75 so that the adjacent apices are substantially aligned. In fact, aligned apices may be selectively attached to each other, for example, with a lock stitch pattern (as shown in FIG. 5H and more fully explained in patent application Ser. No. 08/538,706, filed Oct. 3, 1995, previously incorporated herein by reference), to greatly reduce axial flexibility where desired. Clearly such selective offsetting of apices will be effective with ring frames, zig-zag coils, and a wide range of alternative stent-graft structures, and continuous graft configurations.

Figure 5F:
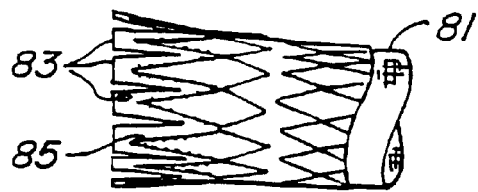
FIGS. 5F–5H illustrates alternative stent-graft sealing structures, according to the principles of the present invention.
Figure 5G:
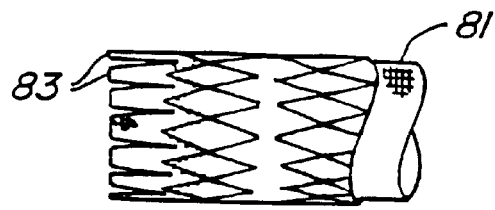
Figure 5H:
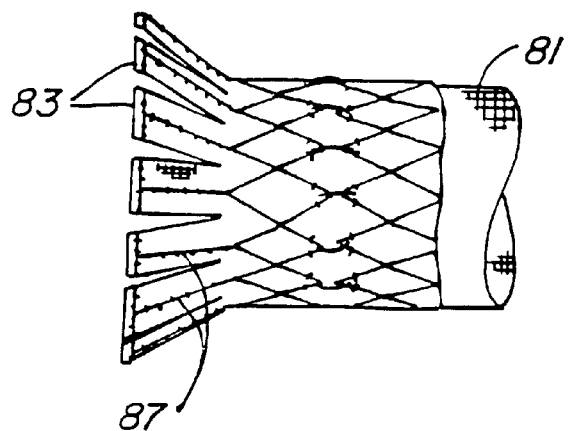

Alternative sealing structures are illustrated in FIGS. 5F–G. Generally, liner 81 is split at one end to form a plurality of sealing flaps 83. Optionally, the sealing flaps are substantially unsupported by the frame. Alternatively, the frame adjacent sealing flaps 83 includes axially elongated members which support the sealing flaps, for example, elongated diamonds 85 or fingers 87. These elongated members (or the sealing flaps themselves) are preferably resiliently biased radially outward, typically by heat setting over a tapered mandrel. In some embodiments, the flaps may fold back along the prosthesis when the prosthesis is compressed for deployment. Regardless, each sealing flap will preferably expand radially outward substantially independently of the other sealing flaps, thereby improving the seal between the end of the prosthesis and a highly irregular body lumen. Optionally more than one row of overlapping sealing flaps may also be used.

Figure 6A:
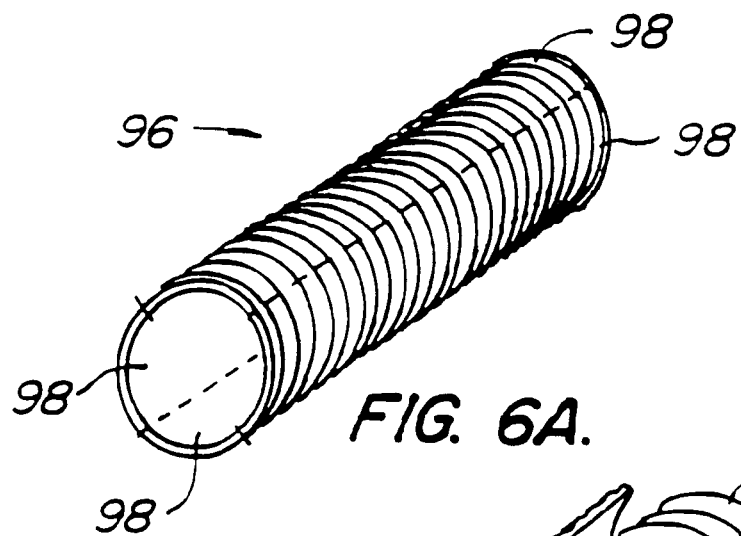
FIGS. 6A–6C illustrate alternative flexible prosthetic structures in which the liner is supported by a plurality of cylindrical segments.
Figure 6B:
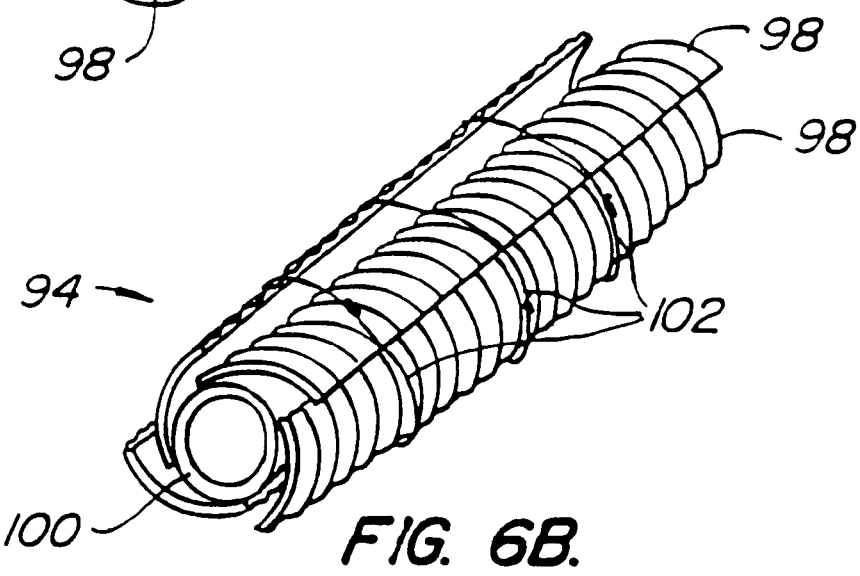
Figure 6C:
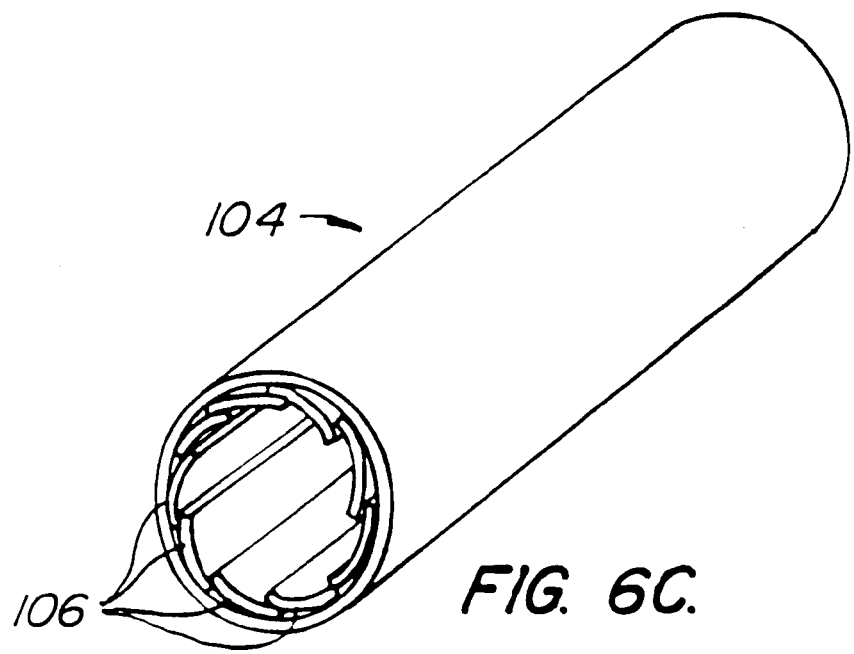

Referring now to FIGS. 6A and B, an alternative flexible prosthetic structure may be fabricated by cutting a cylindrical corrugated polyester graft 96 into a series of cylindrical segments. The cylindrical segments may then be used as reinforcing elements by attaching them axially along an expansible tube 100. Suitable expansible tubes may be formed from partially oriented yarn, polypropylene, polyethylene, annealed polyester, PTFE, or the like. The reinforcing elements are preferably free to slide over each other as the liner is expanded in situ, and provide some column strength, hoop strength, and kink resistance while also allowing the reinforced lumen to flex axially.

Optionally, a plurality of expansible fibers or yarns 102 could be wrapped around the exterior of the corrugated graft segments to hold the structure in a compact profile, and yet still allow expansion. Alternatively, outer fibers 102 may be frangible, breaking under a predetermined force to allow the prosthesis to be expanded in situ to the desired size. An internally supported flexible structure 104 having similar internal reinforcing elements 106 may optionally avoid the use of the external wrapping yarns.

A particularly advantageous flexible prosthetic structure 110 will be described with reference FIGS. 7A–G. Flexible structure 110 comprises a radially expandable liner 112 supported by a plurality of ring frames 114. A series of connector elements 116 extend between adjacent ring frames 114. Optionally, connector elements 116 may also be used to support the liner 112. Advantageously, the connector elements and ring frames may be independently optimized to tailor the mechanical properties of the prosthesis structure, particularly for use as a flexible trunk or branch position in the branching prosthesis of FIG. 3A. Alternatively, flexible prosthetic structure 110 may find use as a stent, or as a cylindrical stent-graft.

Preferably, the ring frames comprise resilient self-expanding structures, ideally comprising a super-elastic shape memory alloy such as Nitinol™. Connectors 116 preferably comprise a malleable material, ideally including martensitic Nitinol™, stainless steel, cobalt-nickel alloy, titanium, or tantalum. Clearly, the connector elements can provide additional column strength to the prosthetic structure, as well as providing support to the liner between the ring frames. Advantageously, such malleable connectors may also provide a structure which will expand resiliently when deployed in situ, and which will conform plastically to an axially tortuous body lumen, such as the blood vessels of the vascular system.

Preferably, connector elements 116 comprise serpentine elements which extend axially between adjacent frame loops. Careful selection of the serpentine shape allows tailoring of the bending properties of the prosthesis. Such serpentine connector elements located at the outer portion of an axial bend in the prosthesis will be straightened, while those at the inner portion will decrease in length, optionally maintaining the axial length of the prosthesis at a relatively constant amount. Alternatively, the connector elements may rely primarily (or solely) on either elongation or compression alone, thereby inducing changes in the length of the prosthesis when bent.

Figure 7A:
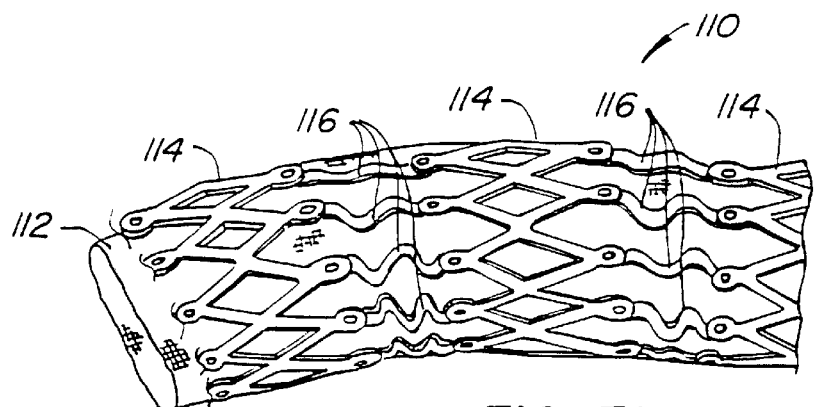
FIG. 7A illustrates an endoluminal prosthetic structure in which a liner is supported by a plurality of self-expanding loops, and in which serpentine malleable connectors extend between adjacent loops, according to the principles of the present invention.
Figure 7B:
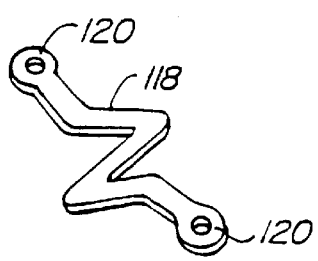
FIGS. 7B–7G show alternative connector structures and connector attachment mechanisms for use in the prosthesis of FIG. 7A.
Figure 7C:
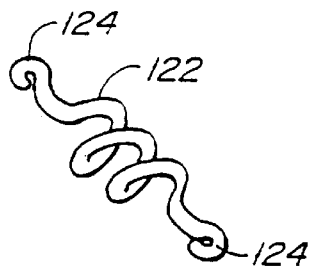
Figure 7D:
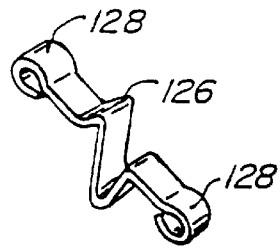

FIGS. 7B–D illustrate alternative connector element structures. A flat connector element 118 may be cut from a flat sheet of the desired malleable material, and optionally includes ends 120 having passages cut therethrough to facilitate attachment of the connector element to the resilient frame structure. Such a flat structure has the advantage of not decreasing the internal prosthetic lumen cross-section within a narrow body lumen, and the flat serpentine shapes may be cut from sheet stock using known laser cutting, lithography techniques, or the like.

Alternatively, a wire connector element 122 having bent loop ends 124 may be formed as a helical coil. In a still further alternative, a bent connector element 126 may be formed from a straight strip of malleable material, as shown in FIG. 7D, and may also include folded ends 128. Clearly, a wide variety of alternative metallic or polymer connector structures may be suitable. Generally, it will be preferable to make use of materials which are both malleable and biocompatible, as described above.

Figure 7E:
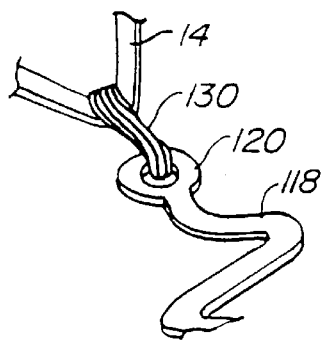
Figure 7F:
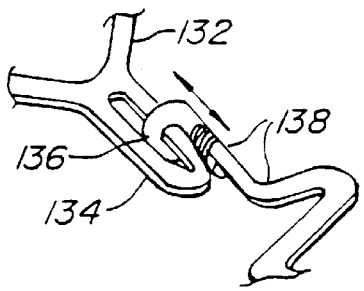
Figure 7G:
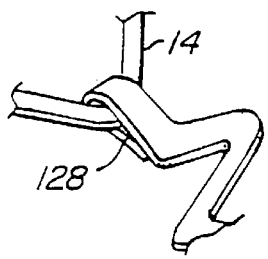

A variety of alternative attachment mechanisms for coupling the frame structure to the connector elements are shown in FIGS. 7E–G, and also in FIG. 7A. Generally, the connector elements may be attached to the frame loops by welding, soldering, adhesive bonding, polymer rivets, suturing, or the like. In some embodiments, it may be possible to utilize members which extend from a resilient frame, and which have been formed to the desired shape and heat treated or otherwise processed to produce the desired malleable properties. In some embodiments, the mechanism used to attach the resilient frame to the connector elements will also attach the liner to the frame, for example, stitching which extends through passages in both the connector elements and the frame, and then through a woven textile liner.

It may be desirable to allow some longitudinal motion between the connector elements and their associated frames without deforming the connector elements. An oversized suture loop 130 between a ring frame 14 and passage 120 of flat connector element 118 provides a limited amount of axial motion. Similarly, an axial slot 134 in a slotted frame 132 provides a precisely controlled amount of axial motion of a loop 136 on a wire connector element 138. Note that loop 136 may further be reinforced by suture, wire, adhesive, or the like. Alternatively, the end of the connector element may be folded over a ring frame 14, and optionally adhesively bonded in place, to provide a positive connection.

Preferably, connectors 116 compress or elongate plastically under forces typical of those imposed on the prosthesis during deployment. As these forces are typically higher than normal physiological forces, the connector elements may advantageously be constructed to avoid deformation from these normal blood and tissue in vivo forces, particularly where a limited amount of axial motion is allowed between connector elements and the ring frames. Therefore, the prosthesis structure can plastically deform during deployment to conform the axis of the prosthesis with the surrounding body lumen, but will thereafter avoid imposing resilient straightening forces against the body lumen.

A method for assembling in situ an endoluminal prosthesis by first positioning and deploying a hub module will be described with reference to FIGS. 8A–E. A branch access catheter 140 is used to insert guidewires 142 down the aorta A and into the left iliac LI and right iliac RI. The branch access catheter 140 preferably comprises a deflecting tip branch access catheter as taught by U.S. Pat. No. 4,774,949, the full disclosure of which is incorporated herein by reference.

A resilient hub module 144 is advanced over both guidewires 142 while compressed within delivery sheath 146. Hub module 144 preferably comprise an elastic sponge-like microporous silicone, silicone foam, low purometer silicone, polyurethane foam or the like, as more fully described in U.S. patent application Ser. No. 08/525,989, filed Sep. 8, 1995, now U.S. Pat. No. 5,769,882, the full disclosure of which is incorporated herein by reference. Hub module 144, which may be stented or unstented, is deployed over guidewires 142 at the luminal intersection I of the aorta A and left and right iliacs LI, RI, optionally extending along the iliacs beyond the aortic aneurysm AA. Ideally, hub module 144 is deployed by a combination of distally advancing pusher shaft 148 and proximally withdrawing catheter sheath 146 so that a trunk portion 150 of the hub module remains within the aorta, while branch portions 152 extend into each of the iliacs. The hub module wall material will preferably be at least in part self-supporting, but may be reinforced adjacent the trunk or branch ports for sealing and to provide sufficient hoop strength to allow prosthetic modules to sealingly engage the hub from within.

Figure 8A:
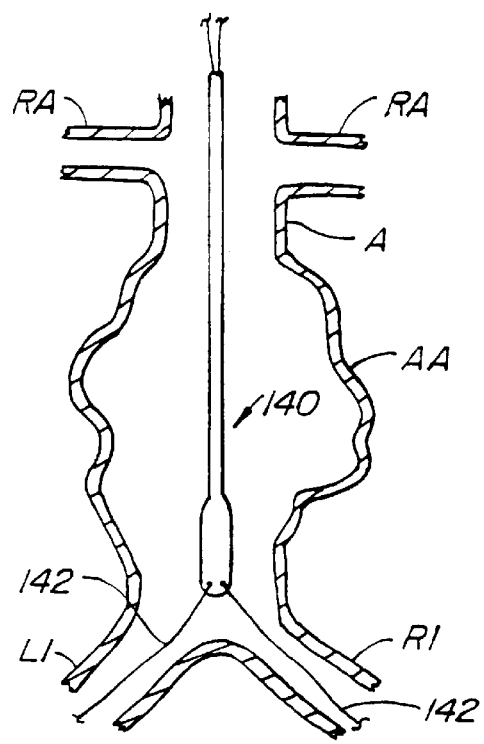
FIGS. 8A–8F illustrate a method for deploying a self-supporting endoluminal hub module within a luminal intersection, according to the principles of the present invention.
Figure 8B:
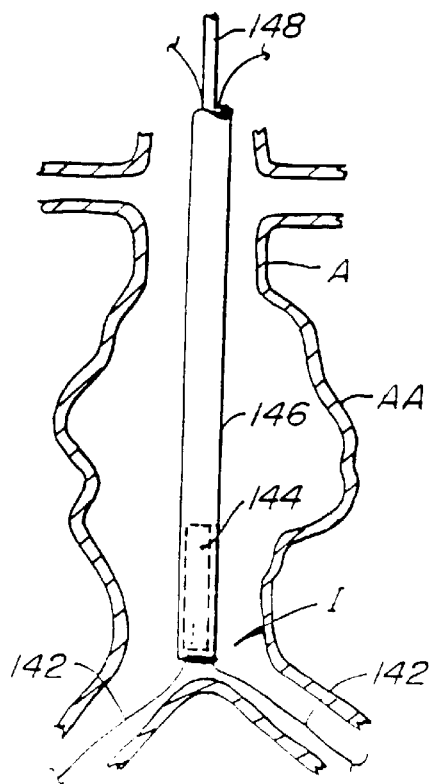
Figure 8C:
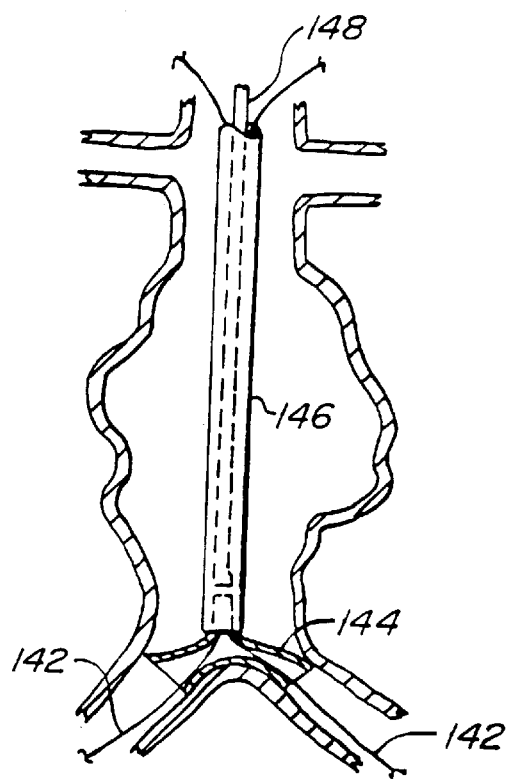
Figure 8D:
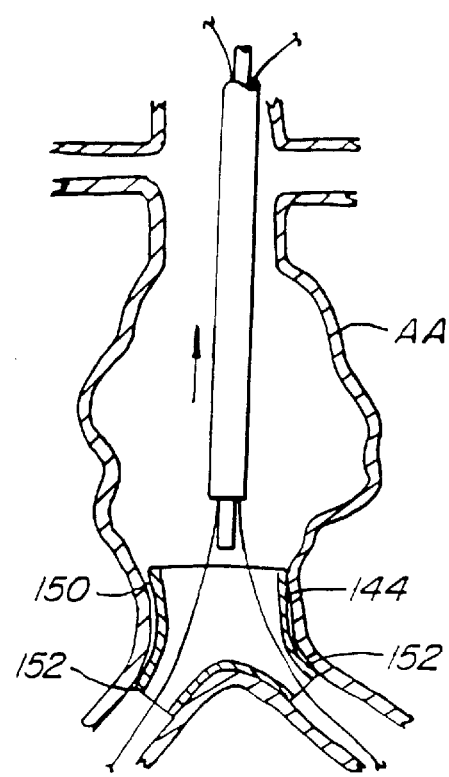
Figure 8E:
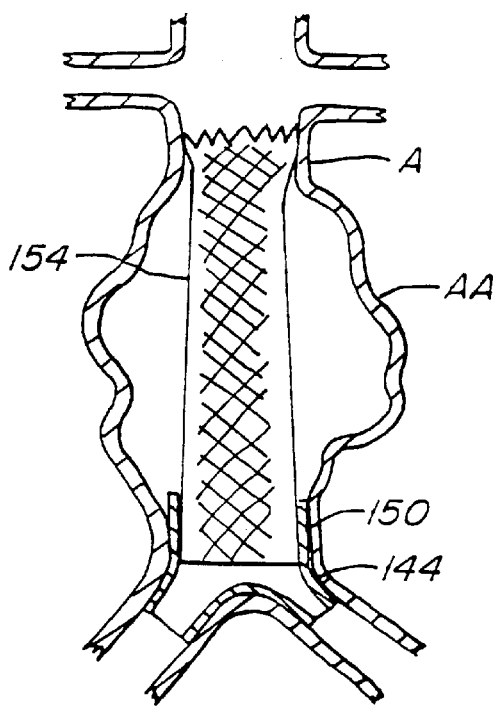
Figure 8F:
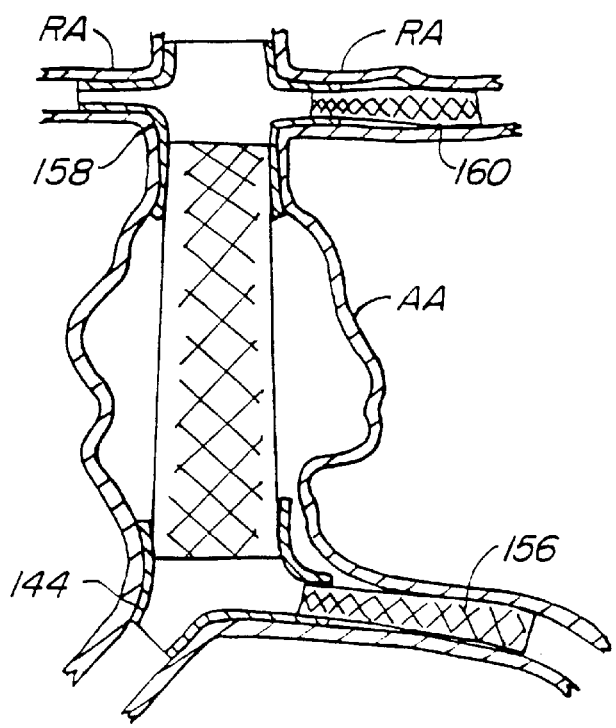
Figure 9A:
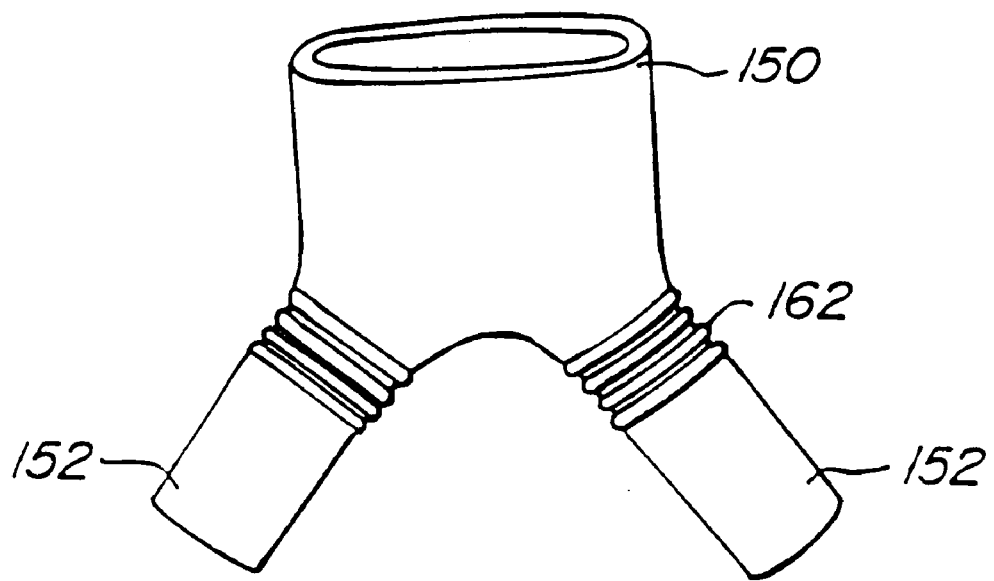
FIGS. 9A–9B illustrate alternative endoluminal hub modules having flexible portions between their trunk and branch portions.
Figure 9B:
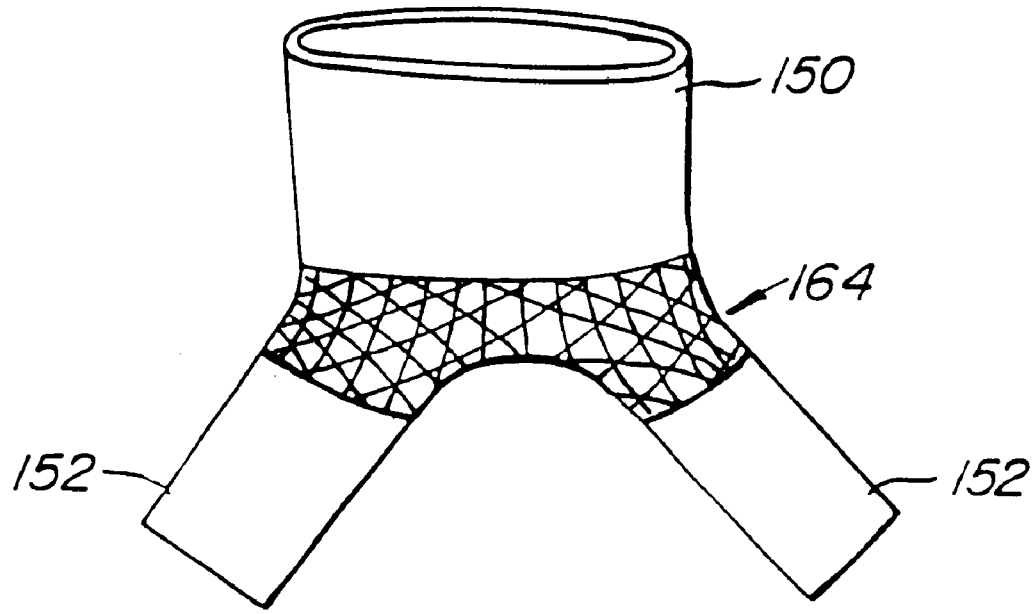

In some embodiments, it may be possible to completely seal off aortic aneurysm AA by positioning a trunk module 154 within trunk port 150 and expanding the trunk module to sealingly engage the hub module and the healthy aorta upstream of the aneurysm, as illustrated in FIG. 8E. In other cases, it may be necessary to extend one or more branch modules 156 along one or both iliac arteries to fully bypass the aneurysm, as illustrated in FIG. 8F. A four branch hub module 158, similar in structure to hub module 144, may find use in sealing off the upper end of an aneurysm which extends to or along the renal arteries, optionally making use of a renal branch module 160 similar to branch module 156 described above. Optionally, one or more hubs may be securely attached to (and deployed with) a trunk stent-graft.

Although the exemplary microporous silicone can adapt to a range of luminal intersection geometries, it may be advantageous to provide a variety of hub modules having differing angles to accommodate a wider variety of vascular geometries, allowing selection of a suitable hub for each patient. In extreme cases, it may even be preferable to custom mold a hub module for a specific patient's vasculature, preferably based on information provided by fluoroscopy, ultrasound, or some other imaging modality.

To increase the ability of the hub module to conform to a variety of vascular geometries, it may be advantageous to include corrugated portions 162 or braided portions 164 between the trunk port 150 and the branch ports 152 as illustrated in FIGS. 9A–D. Such corrugated structures accommodate compression along the inside of a tight bend radius without kinking, while braided structures are inherently kink resistant when bent. Similar enhanced flexibility portions may be used at the junctions of a trifurcation to increase the conformability of an aortal renal hub module, similar to renal hub module 158 shown in FIG. 8F. Advantageously, first deploying the hub module adjacent the intersection of the aorta and iliac arteries allows the trunk module to be supported at least in part from the luminal intersection, particularly during deployment.

Figure 10A:
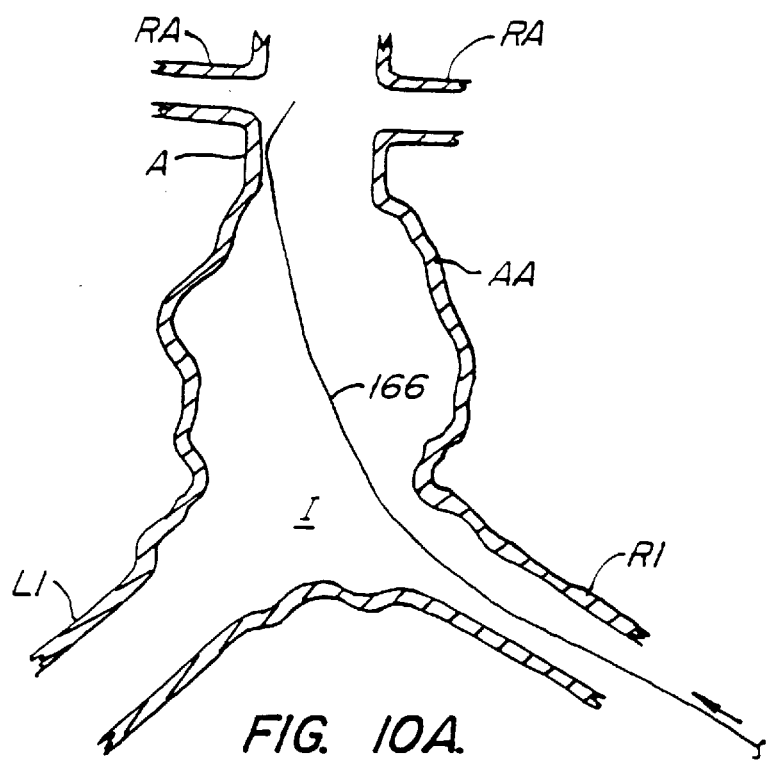
FIGS. 10A–10C illustrate a method for positioning guide wires adjacent to a luminal intersection to promote precise positioning of an endoluminal prosthesis by selectively tensioning opposed guide wire ends, according to the principles of the present invention.
Figure 10B:
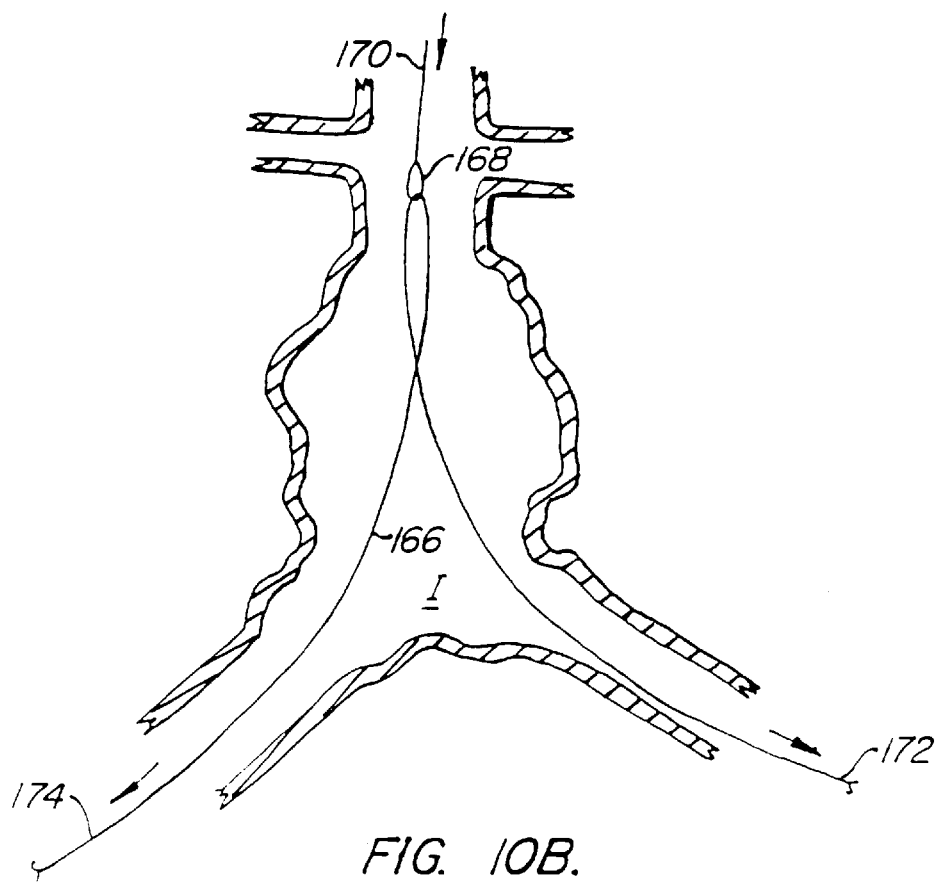
Figure 10C:
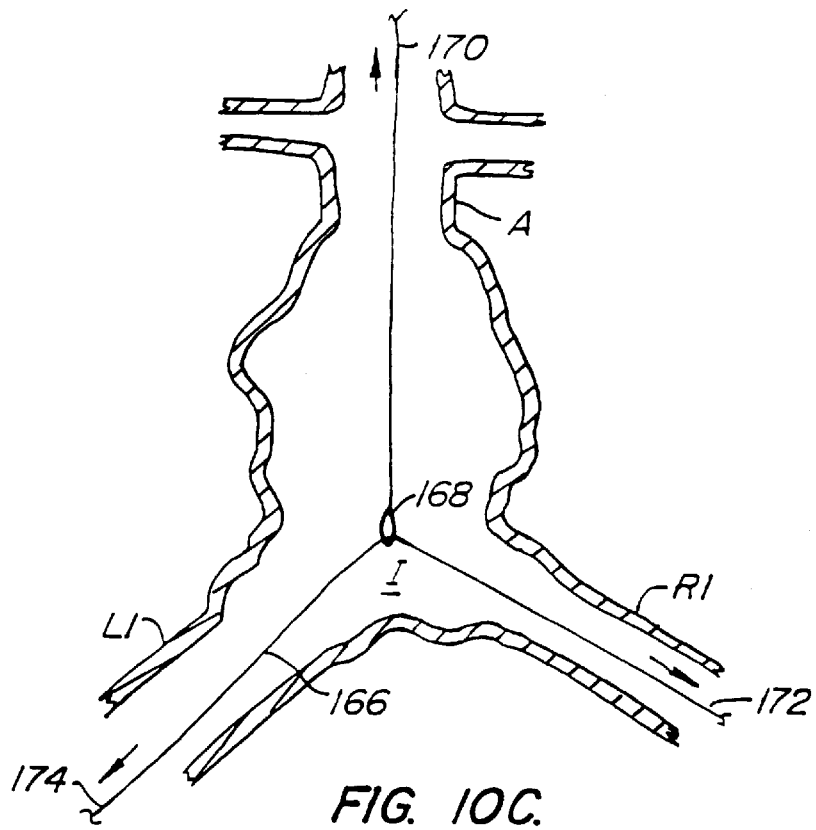

A method for precisely positioning an endoluminal prosthesis using guidewires which pass through the luminal intersection will be described with reference FIGS. 10A–C. In the exemplary method, a guidewire 166 is introduced from an inferior position and advanced along the right iliac, RI beyond the luminal intersection I, through the aorta A to the subclavian or carotid artery, where the guidewire is extended out of the patient body. Guidewire 166 can then be threaded through a loop 168 in a second guidewire 170, and the distal end of guidewire 166 be again maneuvered back through the aorta, beyond the luminal intersection I, along one of the iliac arteries, and again extended out of the patient body.

Advantageously, a proximal end 172 and distal end 174 of guidewire 166 may be selectively tensioned to advance second guidewire 170 down the aorta to the luminal intersection I. Optionally, guidewire 166 may be fed inward and outward through the same iliac to allow loop 168 to be positioned relative to the aortic and one of the two iliac arteries. Alternatively, as shown in FIG. 10C, guidewire 166 may be fed inward through, and outward from, alternative iliac arteries. In either case, tensioning the proximal and distal ends of guidewire 166 and the proximal end of second guidewire 170 precisely positions hoop 168 relative to the luminal intersection I. Hence, this method provides multiple points of control and access to fine tune endoluminal prosthesis placement, and allows prosthetic modules to be advanced along either end of guidewire 166 or along second guidewire 170 to the precisely positioned loop 168.

As described above, many bifurcated stent-graft systems depend on attachment to a narrow healthy or less diseased zone between the renal arteries and the upstream end of the aneurysm. The length and diameter of this healthy zone can be very difficult to predict, making secure attachment and sealing of the endoluminal prosthesis problematic. As there may be little or no healthy aorta remaining between the aneurysm and the renal arteries to anchor a branching endoluminal prosthesis, it would be advantageous to find alternative support mechanism for branching endoluminal prostheses.

As was also described above, the iliac arteries may define substantial angles relative to the aorta, particularly on patients having abdominal aortic aneurysms. This often complicates the positioning of a tightly compressed (and therefore relatively stiff) endoluminal prosthesis across the lumenal intersection from the aorta to the iliac arteries.

Figure 11A:
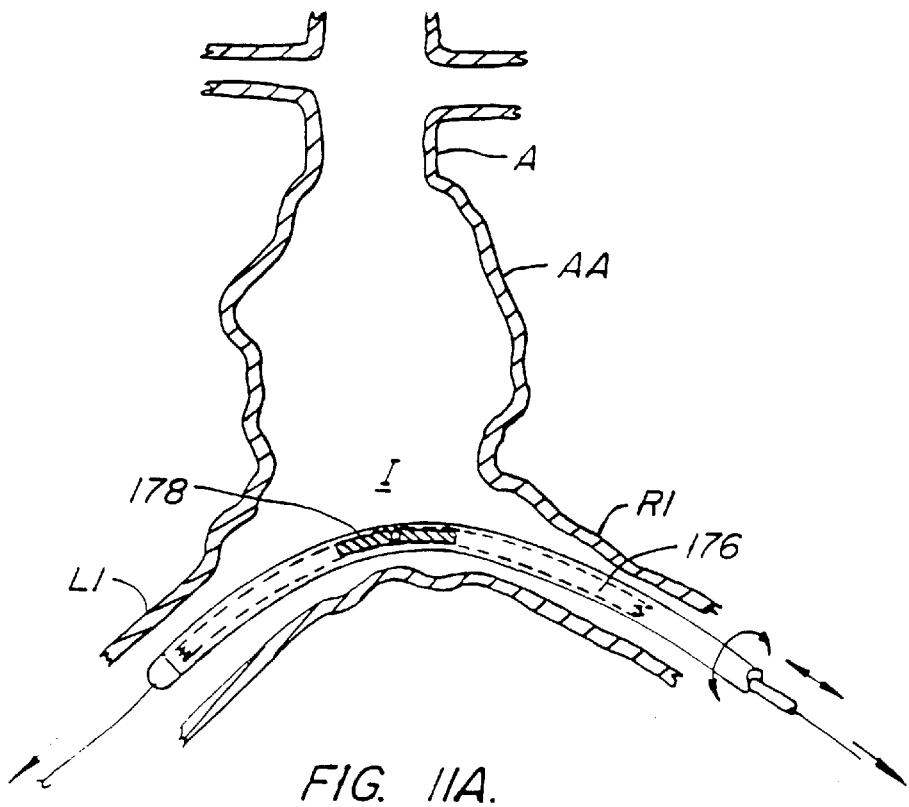
FIGS. 11A–11C illustrate a method for deploying a branching endoluminal prosthesis by first deploying a branch module which extends across the trunk lumen and extending into opposing branch lumens, and by then deploying a trunk module within a trunk port of the branch module, according to the principles of the present invention.
Figure 11B:
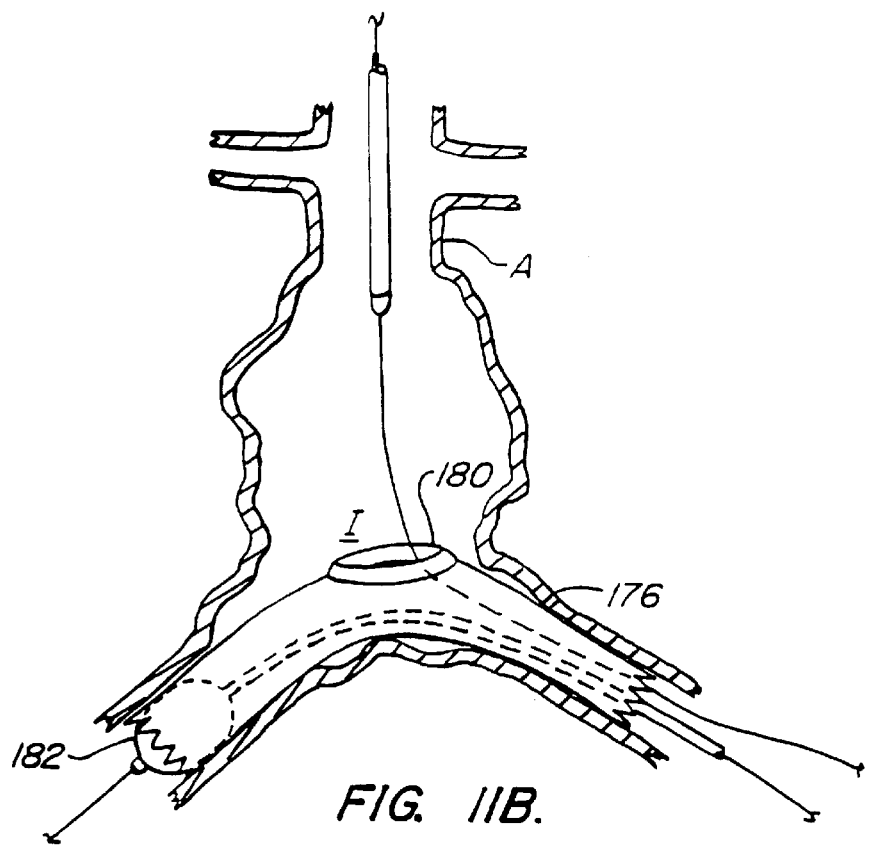
Figure 11C:
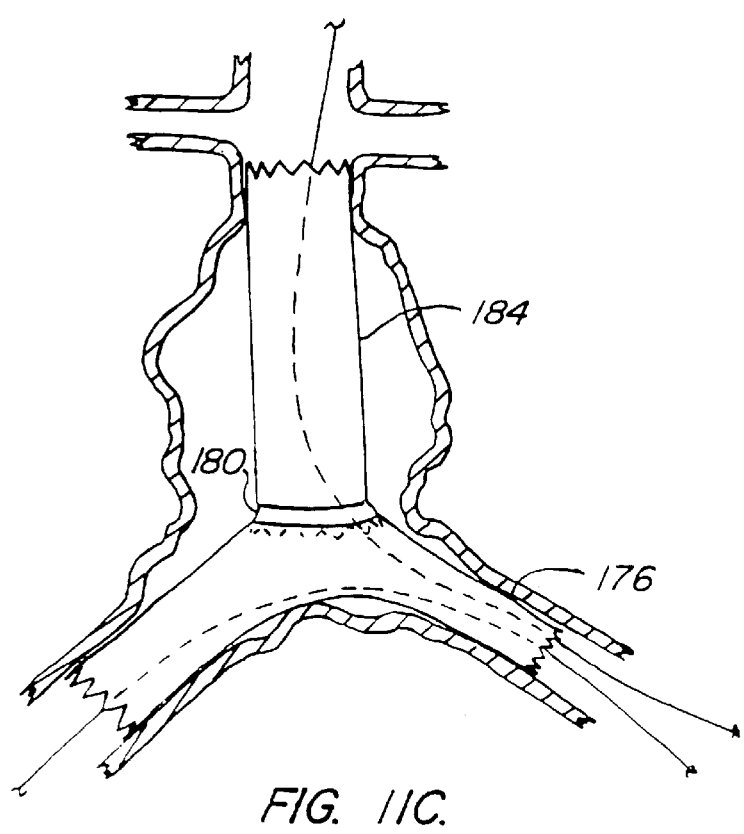

For these reasons, it may be advantageous to instead position and deploy a branch module 176 extending across the luminal intersection I from the right iliac to the left iliac, as illustrated in FIG. 11A. Branch module 176 will generally include a trunk port 180 which is preferably oriented along the aorta, as shown in FIG. 11B. Such orientating of prosthetic modules is aided by a radiographic marker 178 which provides a visual representation of the expanded module under imaging. Optionally, a balloon catheter 182 may be used to hold branch module 176 in position during deployment of a trunk module 184 into sealing engagement with trunk port 180.

Figure 12:
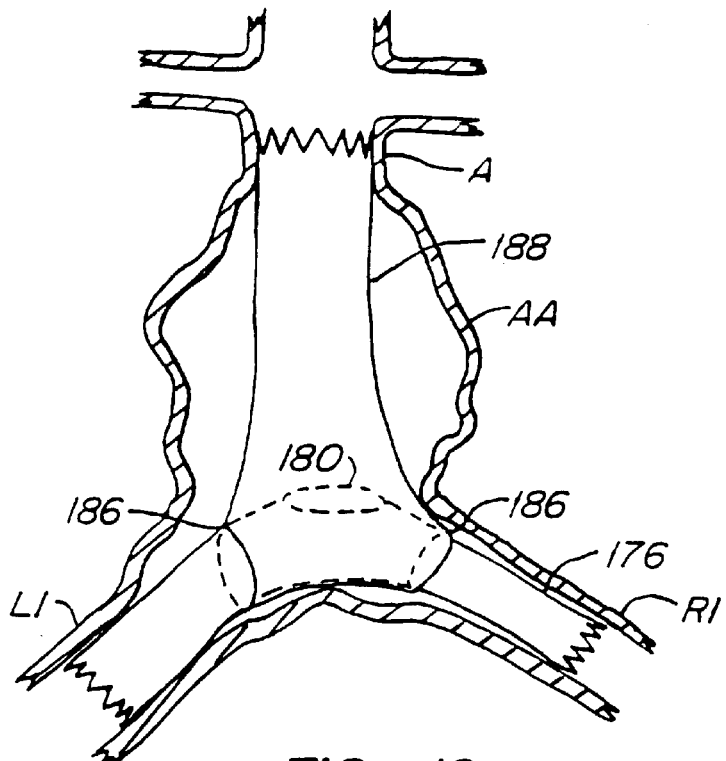
FIG. 12 illustrates an alternative branching endoluminal prosthesis in which a branch module is positioned through a deployed trunk module, according to the principles of the present invention.
Figure 13:
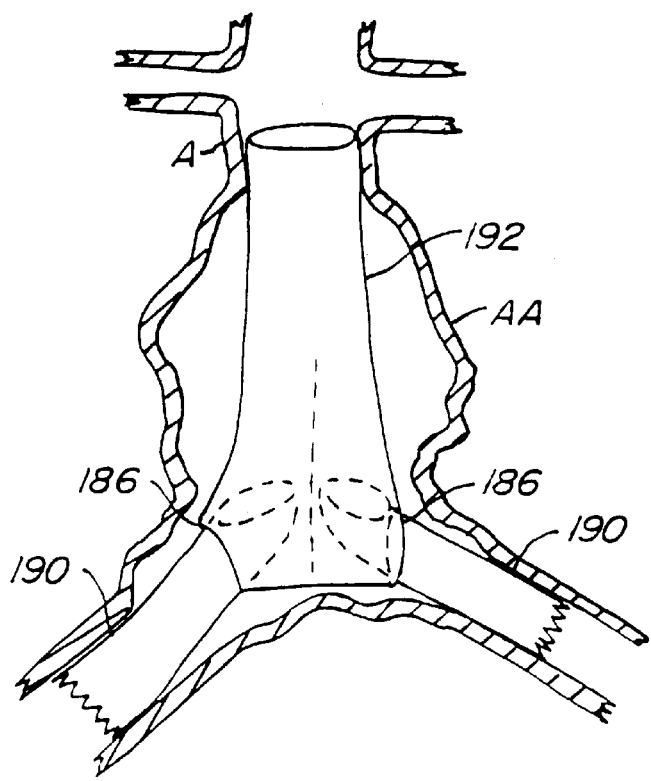
FIG. 13 illustrates an alternative branching inner luminal prosthesis in which independent branch modules are deployed within an expanded trunk module.

Referring now to FIG. 12, branch module 176 may alternatively be deployed through branch ports 186 of a previously deployed primary trunk module 188. Flow for the two iliacs thus enters the branch module within the lumen of primary trunk module 188 through trunk port 180. A somewhat similar arrangement, which makes use of independent branch modules 190 that sealingly engage an alternative primary trunk module 192 at branch ports 186, is illustrated in FIG. 13.

Figure 14A:
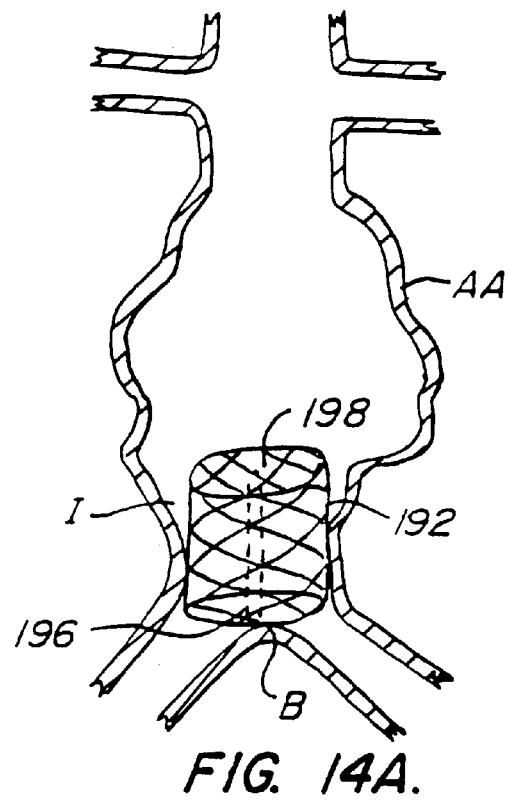
FIGS. 14A–14B illustrate a method for deploying a branching endoluminal prosthesis in which a spacer module is first deployed to provide support for the trunk module from adjacent to the branch lumens of the body lumen system.
Figure 14B:
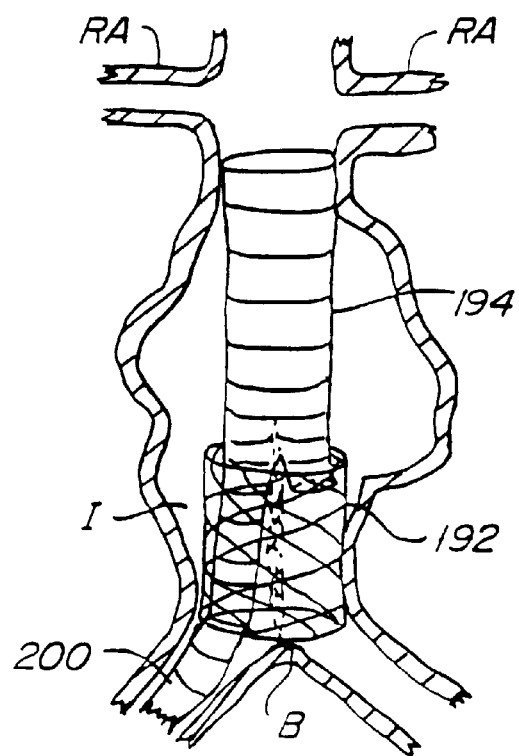

It would be advantageous to provide still further alternative methods for supporting the endoluminal prosthesis assembly, rather than relying substantially on the aorta below the renals. As illustrated in FIGS. 14A–B, a spacer module 192 may first be deployed adjacent the luminal intersection I, preferably with a lower surface 196 in contact with the bifurcation B of the body lumen system. Spacer module 192 is selected so that an upper surface 198 is at the proper distance from the lower surface 196 so that a bifurcated trunk module 194 resting on upper surface 198 is correctly positioned just downstream of the renal arteries. Branch modules may then be positioned through the spacer module and into the branch ports of the bifurcated trunk module to complete the bifurcated prosthesis assembly. Clearly, one or more of the branch portions may optionally be formed integrally with the trunk portion, within the scope of the present invention.

Figure 15A:
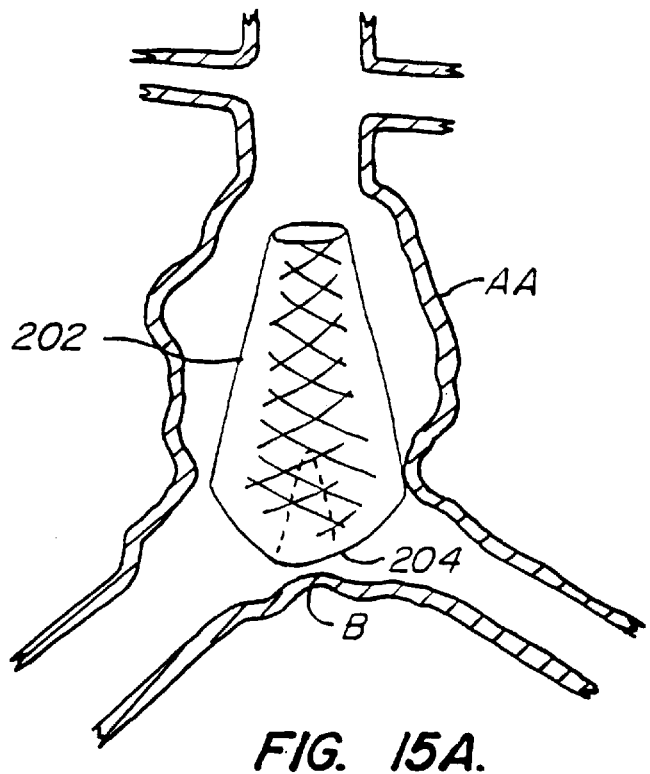
FIGS. 15A–15B illustrate a method for deploying a branching prosthesis in which a tapering primary module is first deployed adjacent a luminal intersection, according to the principles of the present invention.
Figure 15B:
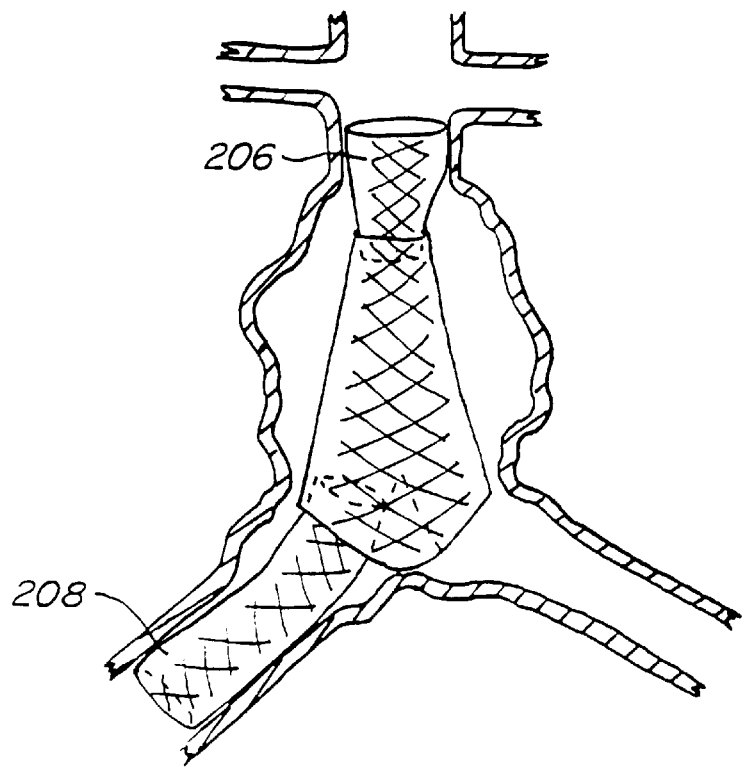

A still further alternative modular prosthetic assembly will be described with reference to FIGS. 15A–B. Tapered primary module 202 includes a wide branch end 204 which is optionally deployed within the luminal intersection so as to be supported by the body lumen bifurcation B. Advantageously, the wide branch end 204 facilitates engaging branch modules 208 from widely divergent iliac arteries, and may also help support a trunk lumen sealing module 206 from the bifurcation of the body lumen, as shown in FIG. 15B.

Figure 16A:
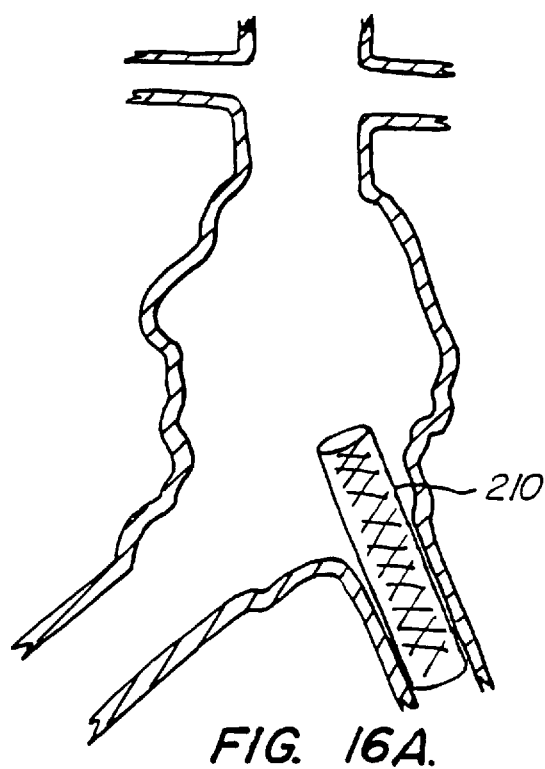
FIGS. 16A–16B illustrate a still further alternative method for deploying a branching endoluminal prosthesis in which the trunk module is deployed within and supported by a previously deployed branch module, according to the principles of the present invention.
Figure 16B:
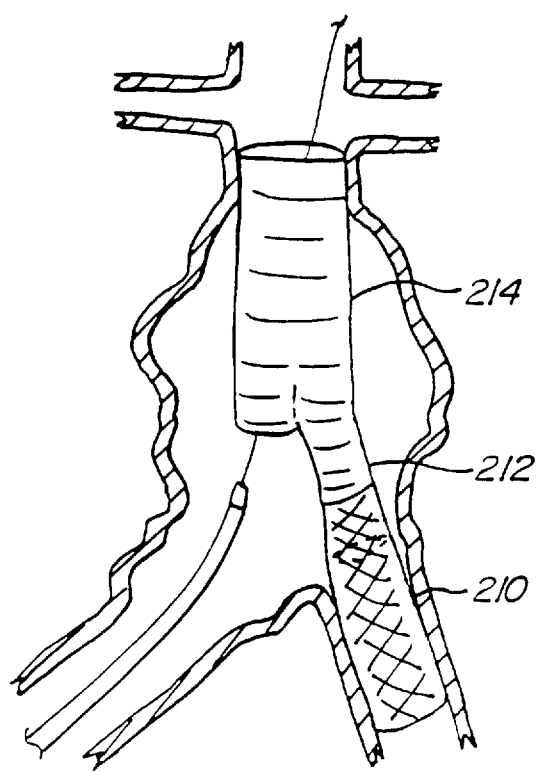
Figure 17A:
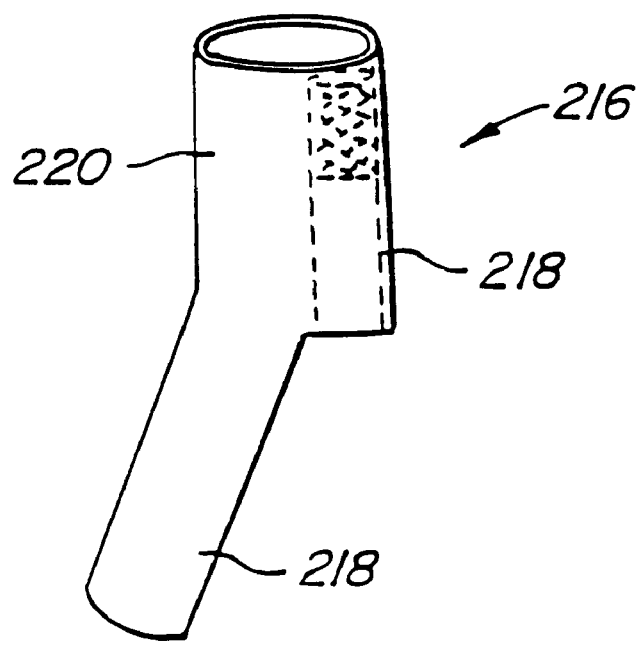
FIGS. 17A–17D illustrate an alternative branching endoluminal prosthesis in which at least one branch portion is compressed within the trunk portion during positioning and deployment.
Figure 17B:
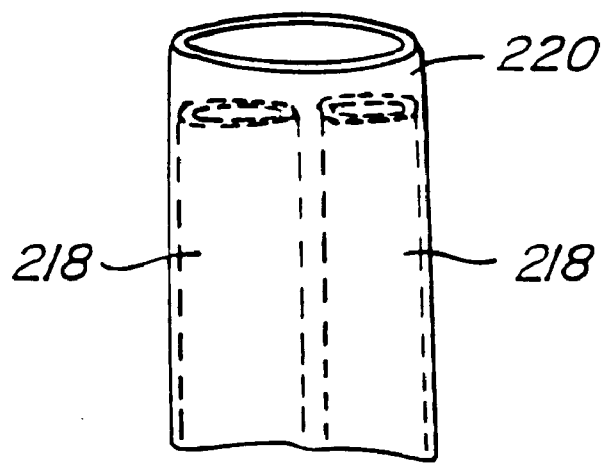
Figure 17C:
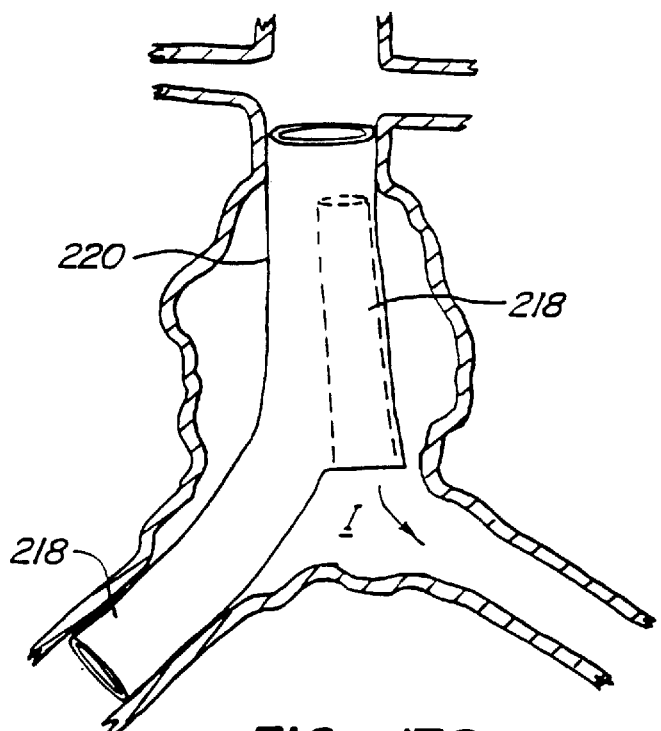
Figure 17D:
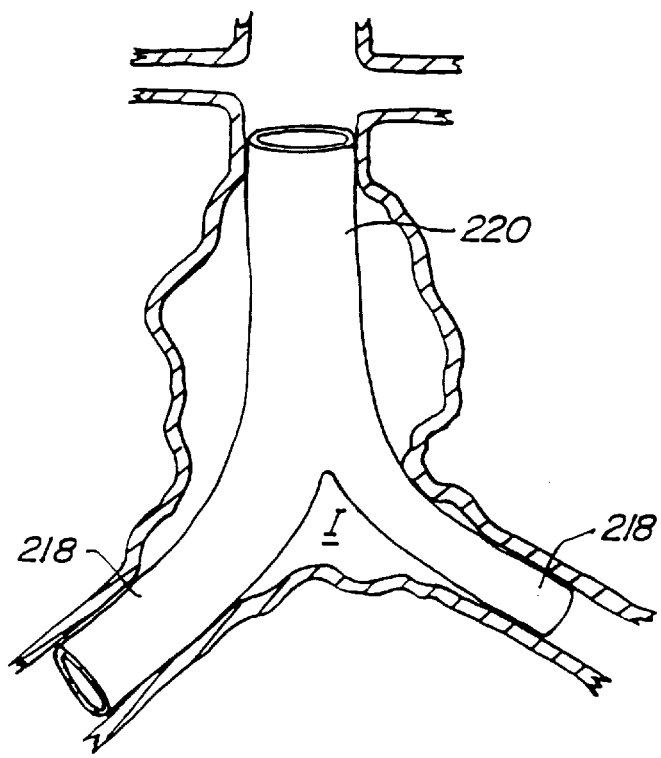

The present invention also provides supporting in situ endoluminal prosthesis assembly from within the iliac, as illustrated in FIGS. 16A–B. In this embodiment, a branch prosthetic module 210 is first deployed within a relatively healthy iliac artery. One branch port 212 of a bifurcated prosthetic module 214 is then positioned and expanded within branch module 210. Optionally, a second branch module is then positioned within an alternate branch port of the bifurcated modules 214, completing the in situ assembly of the bifurcated prosthesis system.

It would be desirable to reduce the number of prosthetic module deployment steps required to deploy an endovascular bifurcated prosthesis system. Toward that end, as shown in FIGS. 17A–D, an extendable leg bifurcated prosthesis 216 may have one or more leg portions 218 disposed within the trunk portion 220 when the prosthesis is radially compressed for positioning and deployment. Optionally, the leg may be everted within the trunk portion, the leg preferably comprising a self-supporting or composite material. Alternatively, the leg may slidingly engage the trunk portion and telescope out into position. In either case, disposing the leg within the trunk portion greatly facilitates positioning the prosthesis across the luminal intersection I.

Figure 18A:
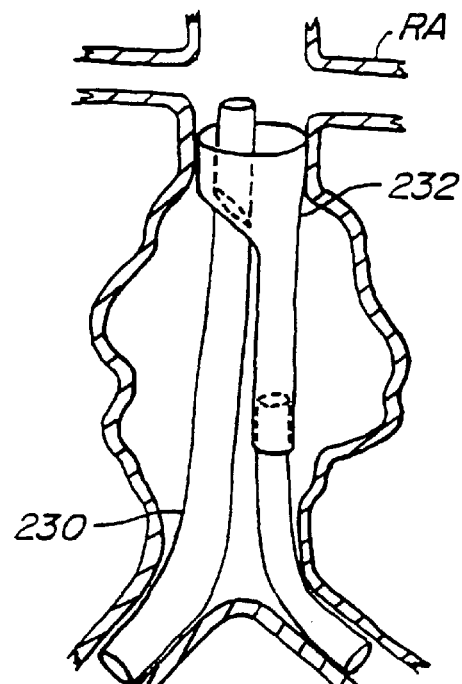
FIGS. 18A–18B illustrate alternative branching endoluminal prosthetic structures having reduced compressed frame volumes and adjustable branch lengths, according to the principles of the present invention.
Figure 18B:
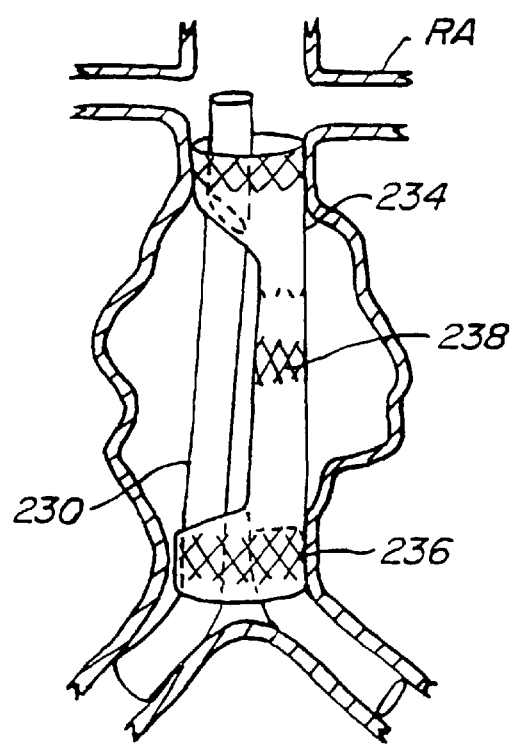

The location and extent of aneurysms along the renal arteries varies considerably between patients, and may at times be difficult to accurately measure. It would therefore be advantageous to provide modular structures adaptable to a wide range of iliac leg positions. The prosthetic assemblies of FIGS. 18A–B achieve such iliac leg placement flexibility by extending a relatively rigid iliac module through bifurcation modules 232, 234, optionally even allowing iliac module 230 to extend in cantilever beyond renal arteries RA. Additionally, by minimizing the length of the trunk lumen portion of the prosthesis, the mass of each module is minimized, facilitating intravascular maneuvering.

To provide some mutual support between the parallel iliac portions, bifurcation module 234 includes a lower support portion 236 having the two-lobed cross-section which is described in patent application Ser. No. 08/538,706 now U.S. Pat. No. 5,824,037, previously incorporated herein by reference. The relatively narrow mid-section 238 allows axial bending of the assembled prosthesis through the aneurysm to adapt to physiological movement.

Figure 19:
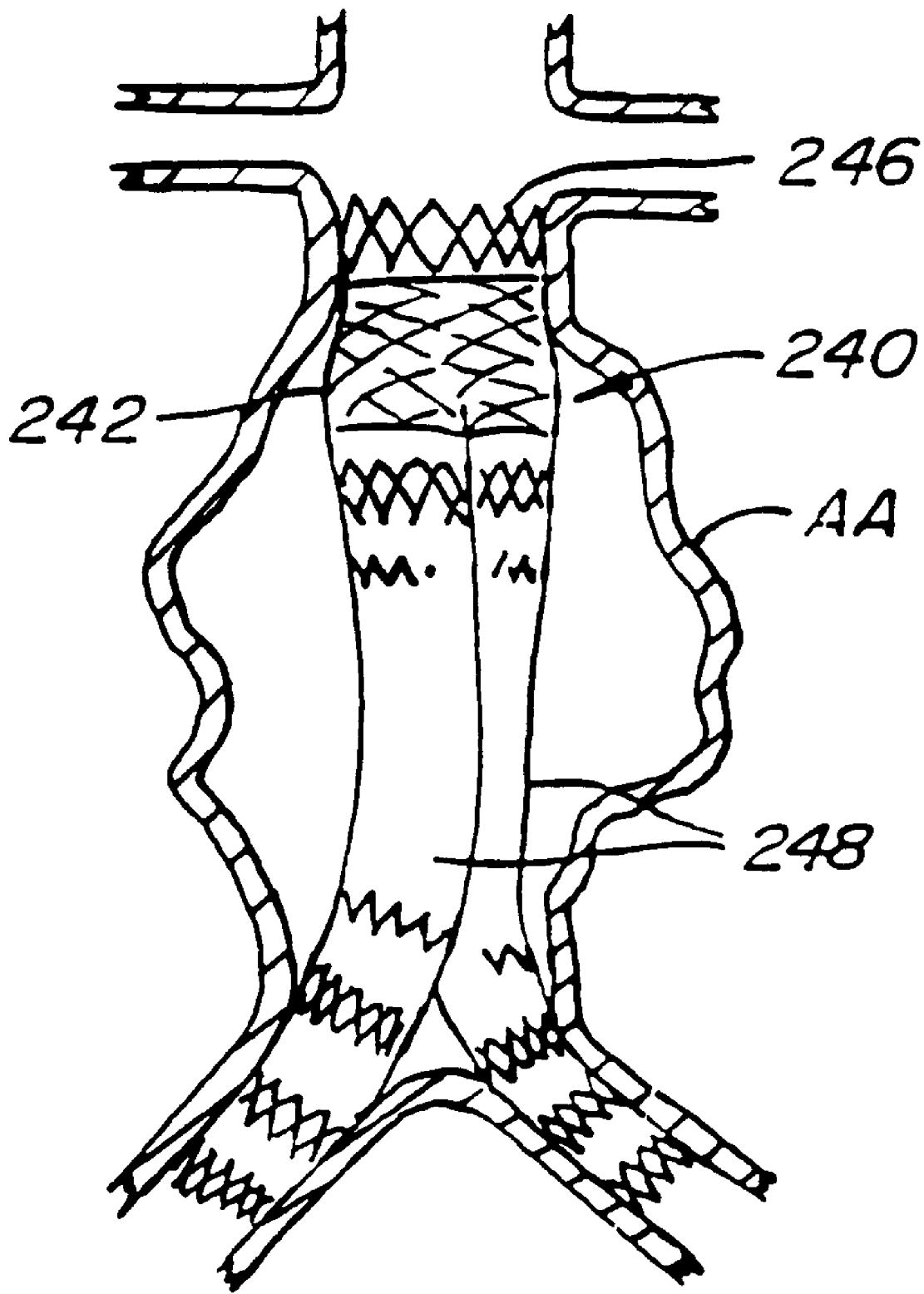
FIG. 19 illustrates a branching endoluminal prosthesis having a short trunk portion to increase overall axial flexibility, according to the principles of the present invention.

Referring finally to FIG. 19, a short trunk branching prosthesis includes a lumen separation portion 242 which is adjacent to a trunk sealing cuff 246, here shown as a single independent ring frame which is crown stitched to the liner. Advantageously, the branch portions 248 will tend to have good axial flexibility due to their significantly smaller diameter than the trunk. Hence, the branch portions may be supported by independent ring-frames.

Although the exemplary embodiments have been described in some detail, by way of illustration and example, the scope of the present invention is limited solely by the appended claims.

What is claimed is:

1. An endoluminal prosthesis comprising:

a plastically expansive tubular liner having a lumen which defines an axis; and an elongatable helical coil supporting the liner, the coil defining a plurality of loops, wherein the loops are separated to enhance axial flexibility of the prosthesis, and wherein the helical coil elongates during plastic expansion of the liner to avoid unwinding of the coil relative to the liner.

2. An endoluminal prosthesis as in claim 1, wherein the liner comprises a polymer tube having integral ribbing disposed between the separated loops of the coil.

3. An endoluminal prosthesis as claimed in claim 1, wherein the coil is attached to the liner at a plurality of attachment points along the length of the coil.

4. An endoluminal prosthesis as claimed in claim 1, wherein the coil comprises a shape memory alloy or a shape memory polymer.

5. The endoluminal prosthesis as in claim 1, wherein the coil comprises linked diamond-shaped elements.

6. The endoluminal prosthesis as in claim 1, wherein the liner material is chosen from a list of materials consisting of: woven polyester such as Dacron, plastically expansible material such as PTFE, partially oriented yarn, annealed composite fiber, and wrapped composite fiber.

7. An endoluminal prosthesis comprising:

a plastically expansible liner material forming a liner tube; and a coil-shaped stent structure having coils separated from each other by a helical separation distance, said coil-shaped stent structure includes a series of linked expandible elements, said coil-shaped stent structure surrounds said liner tube, wherein said liner tube is attached to said coil-shaped stent structure at a plurality of attachment locations around a perimeter of said liner tube such that when said liner tube is expanded, said series of linked expandible elements are stretched between said plurality of attachment locations.

8. The endoluminal prosthesis of claim 7, wherein said series of linked expandible elements are a series of linked diamond-shaped elements.

9. The endoluminal prosthesis of claim 7, wherein said helical separation distance is sized to allow said liner material to flex.

10. The endoluminal prosthesis of claim 7, wherein said liner tube comprises a polymer tube having integral ribbing disposed between adjacent turns of said coils.

11. The endoluminal prosthesis of claim 7, wherein said coil-shaped stent structure is made of a self-expanding material.

12. The endoluminal prosthesis of claim 11,
wherein said self-expanding material comprises a shape memory alloy or a shape memory polymer.

13. The endoluminal prosthesis of claim 7,
wherein said liner material is chosen from a list of materials consisting of: woven polyester such as Dacron, plastically expansible material such as PTFE, partially oriented yarn, annealed composite fiber, and wrapped composite fiber.

14. The endoluminal prosthesis of claim 7,
wherein said coil-shaped stent structure is made of a malleable material.

* * * * *